(12) United States Patent
Lan et al.

(10) Patent No.: US 11,684,656 B2
(45) Date of Patent: Jun. 27, 2023

(54) COMBINATION THERAPY FOR MALIGNANT DISEASES

(71) Applicant: Taipei Veterans General Hospital, Taipei (TW)

(72) Inventors: Keng-Li Lan, Taipei (TW); Yi-Sheng Shih, Taipei (TW); Keng-Hsueh Lan, Taipei (TW); Sung-Hsin Kuo, Taipei (TW); Weng-Shiang Chen, Taipei (TW)

(73) Assignee: TAIPEI VETERANS GENERAL HOSPITAL, Taipei (TW)

( * ) Notice: Subject to any disclaimer, the term of this patent is extended or adjusted under 35 U.S.C. 154(b) by 770 days.

(21) Appl. No.: 15/773,433

(22) PCT Filed: Nov. 4, 2016

(86) PCT No.: PCT/CN2016/104763
§ 371 (c)(1),
(2) Date: May 3, 2018

(87) PCT Pub. No.: WO2017/076360
PCT Pub. Date: May 11, 2017

(65) Prior Publication Data
US 2018/0319861 A1    Nov. 8, 2018

Related U.S. Application Data

(60) Provisional application No. 62/250,984, filed on Nov. 4, 2015.

(51) Int. Cl.
| | | |
|---|---|---|
| *A61K 39/00* | (2006.01) | |
| *A61K 39/395* | (2006.01) | |
| *C07K 16/28* | (2006.01) | |
| *A61K 38/17* | (2006.01) | |
| *C07K 14/705* | (2006.01) | |
| *A61K 39/39* | (2006.01) | |

(52) U.S. Cl.
CPC ...... *A61K 39/0011* (2013.01); *A61K 38/1774* (2013.01); *A61K 39/39* (2013.01); *A61K 39/3955* (2013.01); *C07K 14/70521* (2013.01); *C07K 14/70596* (2013.01); *C07K 16/2818* (2013.01); *A61K 2039/505* (2013.01); *A61K 2039/53* (2013.01); *C07K 2317/76* (2013.01)

(58) Field of Classification Search
None
See application file for complete search history.

(56) References Cited

U.S. PATENT DOCUMENTS

2012/0328693 A1* 12/2012 Lan .................. A61P 37/04
424/450

OTHER PUBLICATIONS

Gunnlaugsson et al (EJC, 45:807-813, 2009).*
Golden et al (CIR, 1(6):365-372, 2013).*
Dewan et al (CCR, 15(17):5379-88, 2009).*
Hiniker et al (NEJM, 266(21):2035-2036, 2012).*
Yoshimoto et al (PLOS, 9(3):e92572, 1-8, 2014).*
Tang et al (CIR, 2(9):831-838, 2014).*

* cited by examiner

*Primary Examiner* — Brad Duffy
(74) *Attorney, Agent, or Firm* — Birch, Stewart, Kolasch & Birch, LLP

(57) ABSTRACT

A new approach for the treatment of a malignant disease is provided. The new method comprises administering a traditional anti-cancer therapy in combination with a DNA or protein vaccine comprising CTLA-4 and PD-1, or a DNA or protein vaccine comprising CTLA-4 and PD-L1.

6 Claims, 25 Drawing Sheets

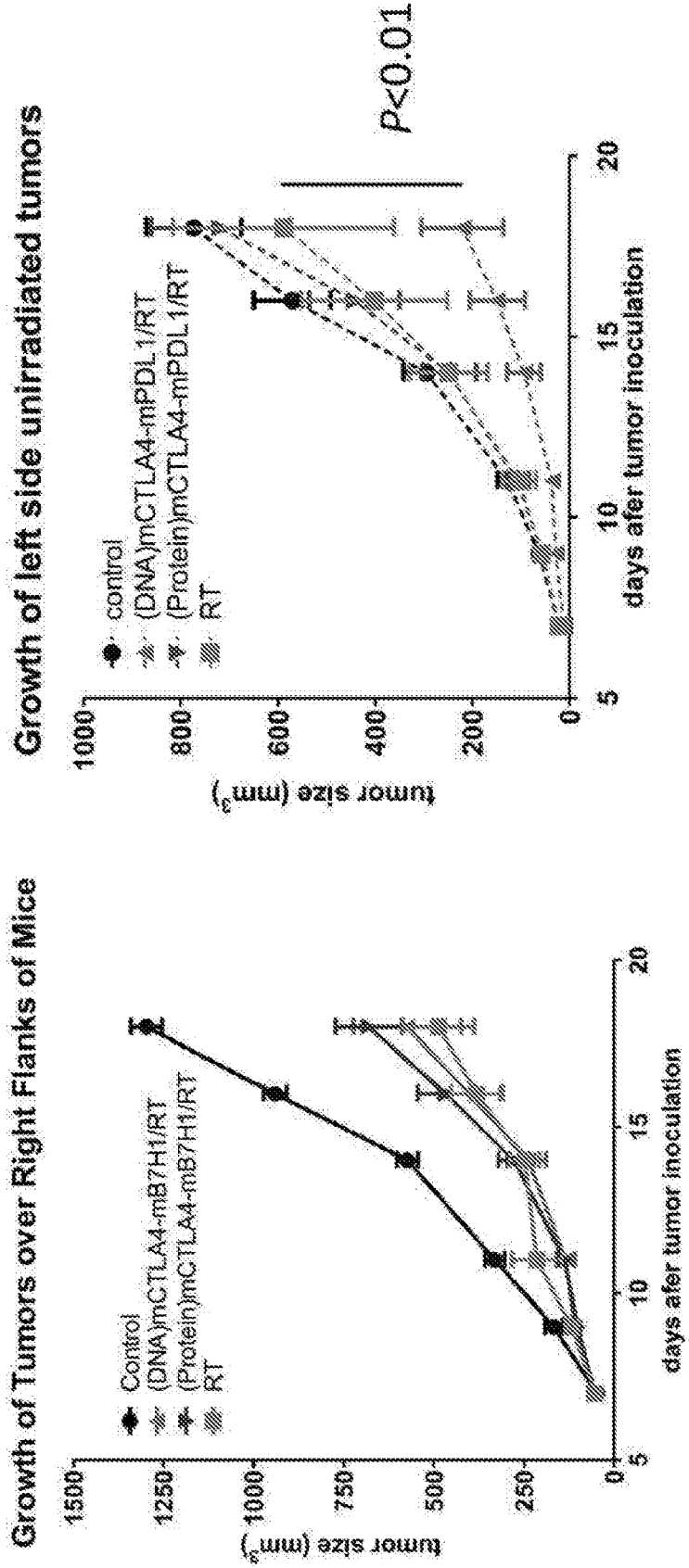
Fig 6B. CTLA-4-PD-L1 DNA vaccine is capable of inducing the abscopal effect after right side tumor received irradiation, as demonstrated by suppressed growth of un-irradiated left side tumors (right panel)

COMBINATION THERAPY FOR MALIGNANT DISEASES

FIELD OF THE INVENTION

The present invention pertains to a new approach for the treatment of a malignant disease.

BACKGROUND OF THE INVENTION

Cytotoxic T-lymphocyte antigen-4 (CTLA-4) was found in 1987 to be a new member of the immunoglobulin superfamily, characterized by domains sharing key structural features with either the variable (V) or the constant (C) immunoglobulin domains (Brunet et al., Nature 328, 267-270). It was elucidated that CTLA-4 played a critical role in regulation of immune system (Keilholz, U., J Immunother 31, 431-439). CTLA-4 was reported to reduce T-cell activation by competing with CD28 for binding site of CD80/CD86 (Rudd et al., Immunol Rev 229, 12-26). Although CTLA-4 protects individuals from autoimmune diseases, it could also suppress anticancer immunity. To avoid the unwanted immune responses caused by CTLA-4 in cancer treatment, several approaches manipulating T-cell costimulatory pathway are being explored to enhance anticancer immune response. Therapy targeting CTLA-4 is one of the most advanced strategies and has revealed promising results in late stage clinical trials (Hodi et al., N Engl J Med 363, 711-723; Hodi, F. S., Asia Pac J Clin Oncol 6 Suppl 1, S16-23; Weber, J., Oncologist 13 Suppl 4, 16-25; and Ribas, A., Oncologist 13 Suppl 4, 10-15). One of the monoclonal antibodies against CTLA-4, ipilimumab, had been granted approval by the FDA in March of 2011 for treatment of metastatic melanoma. In addition to metastatic melanoma, CTLA-4 antibodies are currently undergoing numerous clinical trials for the treatment of malignancies including, pancreatic cancer, colorectal cancer, hepatocellular carcinoma, lymphoma, hormone refractory prostate cancer, ovarian cancer and acute myeloid leukemia.

Program death-1 (PD-1) is a member of the CD28 superfamily which triggers negative signaling pathway upon binding to its ligands, program death ligand 1 and 2 (PD-L1 and PD-L2) (Riley, J. L., Immunol Rev 229, 114-125). The interaction between PD-1 and its ligands leads to inhibition of proliferation, cytokine production, and cytolytic function of T-cell, thereby exhausting T-cell and suppressing its immune response. The PD-1/PD-L pathway plays an important role in tolerance and immunity. It protects tissues and organs from immune-mediated damage. However, this pathway has been shown to be utilized by pathogens of chronic infection and tumors to suppress antimicrobial and anticancer immunity. Given immune-modulating activity of PD-1/PD-L axis, therapeutics targeting this pathway has been developed for treatment of diseases ranging from infections, autoimmunity to cancers (Weber, J., Semin Oncol 37, 430-439).

A new approach for anticancer treatments by enhancing immunity while avoiding suppression of immune responses is still needed.

BRIEF SUMMARY OF THE INVENTION

Accordingly, the present invention provides a combination therapy for a malignant disease with a traditional anti-cancer therapy in combination of a DNA or protein vaccine, which exhibits unexpected improved efficacy in repression of tumor growth.

In one aspect, the present invention provides for treating a malignant disease in a subject, comprising administering to said subject a vaccine in combination with an anti-cancer therapy, in which the vaccine is a pharmaceutical composition comprising a DNA construct or fusion protein comprising a Cytotoxic T-lymphocyte antigen-4 (CTLA-4), and a programmed death-1 (PD-1) or a programmed cell death 1 ligand 1 (PD-L1), or combination thereof.

In another aspect, the present invention provides a pharmaceutical composition for enhancing immune response in a subject under the treatment of a malignant disease, comprising a DNA vaccine comprising CTLA-4 and PD-1, or a DNA vaccine comprising CTLA-4, and PD-L1.

In one embodiment of the invention, the DNA vaccine is a combination of a DNA vaccine of CTLA-4 and a vaccine of PD-L1, or a vaccine of CTLA-4–PD-L1.

In another embodiment of the invention, the DNA vaccine is a combination of a DNA vaccine of CTLA-4 and a vaccine of PD-1, or a vaccine of CTLA-4–PD-1.

In further embodiment of the invention, the vaccine is the vaccine targeting PD-1 fragment (PD1 Frag), CTLA-4–PD-L1 (CTLA4–PDL1 Elec), or CTLA-4–PD-L1 fusion protein.

In a further aspect, the invention provides a method for treating a malignant disease in a subject, comprising administering to said subject with an anti-cancer therapy in combination of a DNA vaccine in combination with an anti-cancer therapy, in which the DNA vaccine is a pharmaceutical composition comprising a DNA construct comprising a polynucleotide sequence encoding Cytotoxic T-lymphocyte antigen-4 (CTLA-4), and a DNA construct comprising a programmed death-1 (PD-1) or a programmed cell death 1 ligand 1 (PD-L1), or combination thereof, or the protein thereof.

In one or more examples of the invention, the anti-cancer therapy is a radiation or anti-cancer antibody treatment.

BRIEF DESCRIPTION OF THE SEVERAL VIEWS OF THE DRAWINGS

For the purpose of illustrating the invention, there are shown in the drawings embodiments. It should be understood, however, that the invention is not limited to the preferred embodiments shown.

In the drawings:

FIG. 6B shows the effects of the DNA vaccine of CTLA-4–PD-L1, which was capable of inducing the abscopal effect after right side tumor received irradiation, as demonstrated by suppressed growth of un-irradiated left side tumors (right panel).

DETAILED DESCRIPTION OF THE INVENTION

Figure 1A:
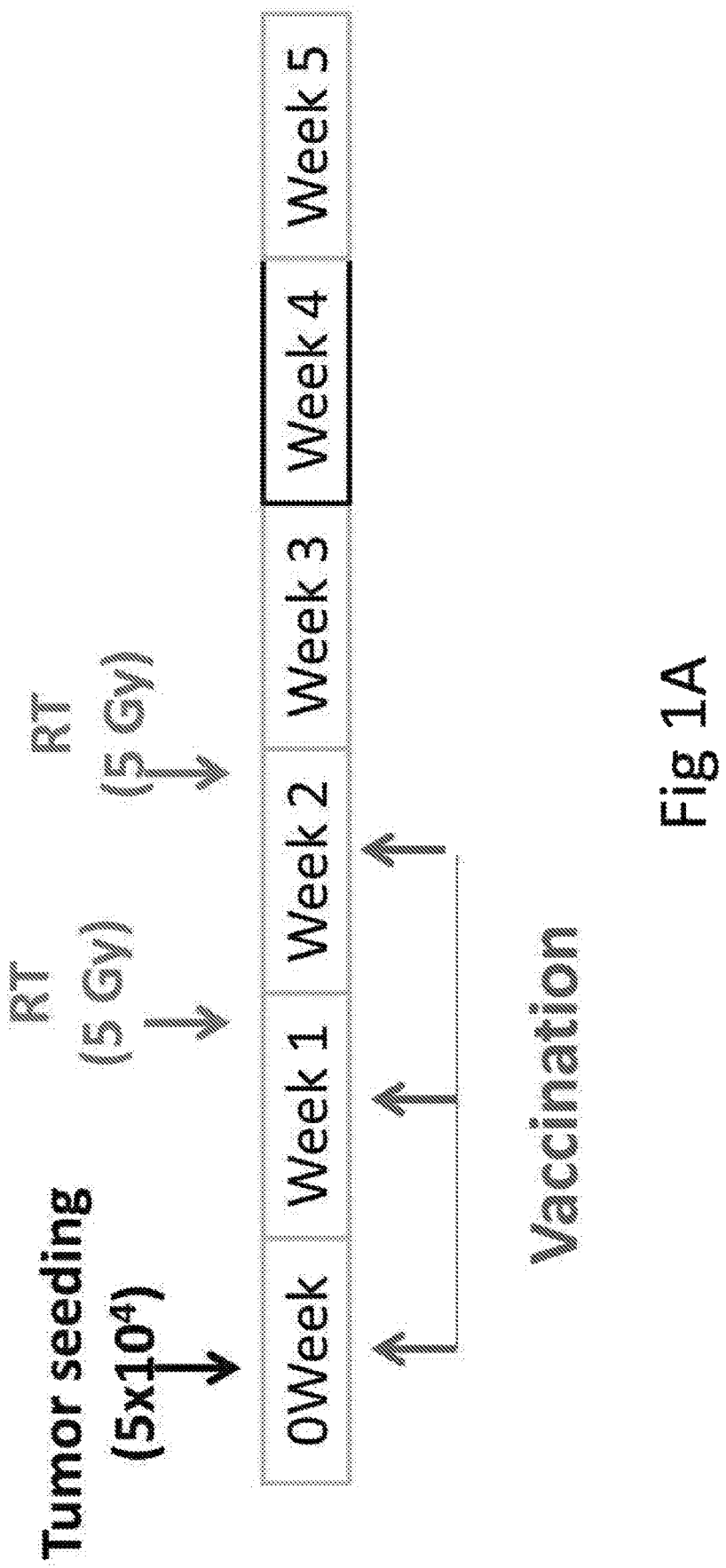
FIG. 1A provides a schema of experiment and treatment schedule used in Examples 1 and 2.

Unless defined otherwise, all technical and scientific terms used herein have the meaning commonly understood by a person skilled in the art to which this invention belongs.

As used herein, the following terms have the meanings ascribed to them unless specified otherwise.

The articles "a" and "an" are used herein to refer to one or more than one (i.e., at least one) of the grammatical object of the article. By way of example, "an element" means one element or more than one element.

The term "encoding" refers to the inherent property of specific sequences of nucleotides in a polynucleotide (e.g., a gene, a cDNA, or an mRNA) to serve as templates for synthesis of other polymers and macromolecules in biological processes having either a defined sequence of nucleotides (i.e., rRNA, tRNA and mRNA) or a defined sequence of amino acids and the biological properties resulting therefrom. Therefore, a gene encodes a protein if transcription and translation of mRNA produced by that gene produces the protein in a cell or other biological system. It is understood by a skilled person that numerous different polynucleotides and nucleic acids can encode the same polypeptide as a result of the degeneracy of the genetic code. It is also understood that skilled persons may, using routine techniques, make nucleotide substitutions that do not affect the polypeptide sequence encoded by the polynucleotides described there to reflect the codon usage of any particular host organism in which the polypeptides are to be expressed. Therefore, unless otherwise specified, a "poly nucleotide encoding an amino acid sequence" includes all polynucleotides that are degenerate versions of each other and that encode the same amino acid sequence. Polynucleotides that encode proteins and RNA may include introns.

The term "vaccine" refers to an agent or composition containing an active component effective to induce a therapeutic degree of immunity in a subject against a certain pathogen or disease. Traditionally, the active component of a vaccine is a polypeptide derived from a pathogen which is the target of the vaccine. The term "DNA vaccine" refers to a vaccine wherein the active component is DNA. The term "protein vaccine" refers to a vaccine wherein the active component is polypeptide.

The term "pharmaceutical composition" refers to a composition suitable for pharmaceutical use in a subject. A pharmaceutical composition comprises an effective amount of an active agent and a pharmaceutically acceptable carrier. The term "effective amount" refers to that amount of an agent effective to produce the intended result, such as the immune response in this invention. The term "pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration). The term "adjuvant" refers to a pharmacological or immunological agent that modifies the effect of other agents (e.g., drugs, vaccines) while having few if any direct effects when given by itself. They are often included in vaccines to enhance the recipient's immune response to a supplied antigen while keeping the injected foreign material at a minimum.

A "subject" is a human or non-human mammal. Non-human mammals include, but are not limited to, primates, ungulates, canines and felines.

A "naked DNA" refers to a DNA construct (for administration to a subject) which is not coupling to liposome.

The pharmaceutical composition of the present invention can be manufactured by conventionally known methods with one or more pharmaceutically acceptable carriers. The term "pharmaceutically acceptable carrier" as used herein encompasses any of the standard pharmaceutical carriers. Such carriers may include, but are not limited to: saline, buffered saline, dextrose, water, glycerol, ethanol and combinations thereof.

The present invention provides a method for treating a malignant disease in a subject, comprising administering to said subject a DNA vaccine in combination with an anticancer therapy, in which the DNA vaccine is a pharmaceutical composition comprising a DNA construct comprising a polynucleotide sequence encoding Cytotoxic T-lymphocyte antigen-4 (CTLA-4), and a DNA construct comprising a programmed death-1 (PD-1) or a programmed cell death 1 ligand 1 (PD-L1), or combination thereof.

In one embodiment of the invention, the anti-cancer therapy may be a radiotherapy or antibody treatment.

The present invention also provides a pharmaceutical combination for enhancing immune response in a subject under the treatment of an malignant disease, comprising a combination of a DNA construct comprising a polynucleotide sequence encoding CTLA-4, and a DNA contract comprising PD-1 or PD-L1, or combination thereof.

Furthermore, the invention provides a method for treating a malignant disease in a subject, comprising administering to said subject a radiotherapy or antibody treatment in combination of a DNA construct comprising a polynucleotide sequence encoding CTLA-4, and a DNA construct comprising PD-1 or PD-L1, or the protein thereof.

According to the invention, the vaccine may be is a combination of a DNA vaccine of CTLA-4 and a vaccine of PD-L1, or a vaccine of CTLA-4–PD-L1. Alternatively, the DNA vaccine may be a combination of a DNA vaccine of CTLA-4 and a vaccine of PD-1, or a vaccine of CTLA-4–PD-1. In addition, the vaccine may be the vaccine targeting PD-1 fragment (PD1 Frag), CTLA-4–PD-L1 (CTLA4–PDL1 Elec), or CTLA-4–PD-L1 fusion protein.

It is approved in the following examples that the DNA-based vaccines targeting immune checkpoint proteins can enhance immune response to tumors. Ionizing radiation, similar to some conventional chemotherapy, possesses immunomodulatory properties. In the invention, the combination with radiation, which may expose tumor-related antigens to the T cells, these immune-modulating DNA vaccines may reverse tumor-induced immune evasion and further create a sustainable anti-tumor immunity.

In embodiments of the instant invention, the subject is treated with an anti-cancer drug, such as an antibody treatment, causing a stimulation of immune response in the subject.

According to the present invention, the malignant disease may be selected from the group consisting of metastatic melanoma, pancreatic cancer, colorectal cancer, hepatocellular carcinoma, lymphoma, hormone refractory prostate cancer, ovarian cancer, acute myeloid leukemia, and lung cancer.

The present invention is further illustrated by the following examples, which are provided for the purpose of demonstration rather than limitation.

Materials

The DNA sequences encoding murine CTLA-4, PD1, or PD-L1 were PCR amplified using a cDNA library obtained respectively from leukocyte of mouse and human as template. The resulting PCR products were fused with a transmembrane domain sequence of placental alkaline phosphatase (PLAP) into a mammalian expression plasmid, pVAC-1, forming CTLA-4 and PD1 or PD-L1 to obtain DNA vaccines.

In vivo studies using 4 animal models with melanoma B16F10, murine colorectal cancer CT26, lung cancer LLC, and hepatoma BNL cells, were conducted.

EXAMPLE 1

Combination Therapy of Radiation Plus DNA Vaccines Targeting CTLA-4 and PD-1 for Melanoma The c58B9BL/6 mice (5 mice/group) were injected with DNA vaccine or control plasmid intramuscularly with the aid of electroporation weekly for 3 times as illustrated in FIG. 1A. One week after the last vaccination, sera from the immunized mice was subjected to ELISA assay for detection of antibody titers against the respective immune checkpoint protein. B16F10 murine melanoma tumors were established on the c58B9BL/6 mice. The radiation regimen used (when applicable) was 2 weekly fractions of 5 Gy after the tumors were established. The mice were divided into groups, each treated with either radiation, radiation plus CTLA-4 vaccine, radiation plus PD-1 vaccine, radiation plus CTLA-4 and PD-1 vaccines, or no treatment (control group).

Figure 1B:
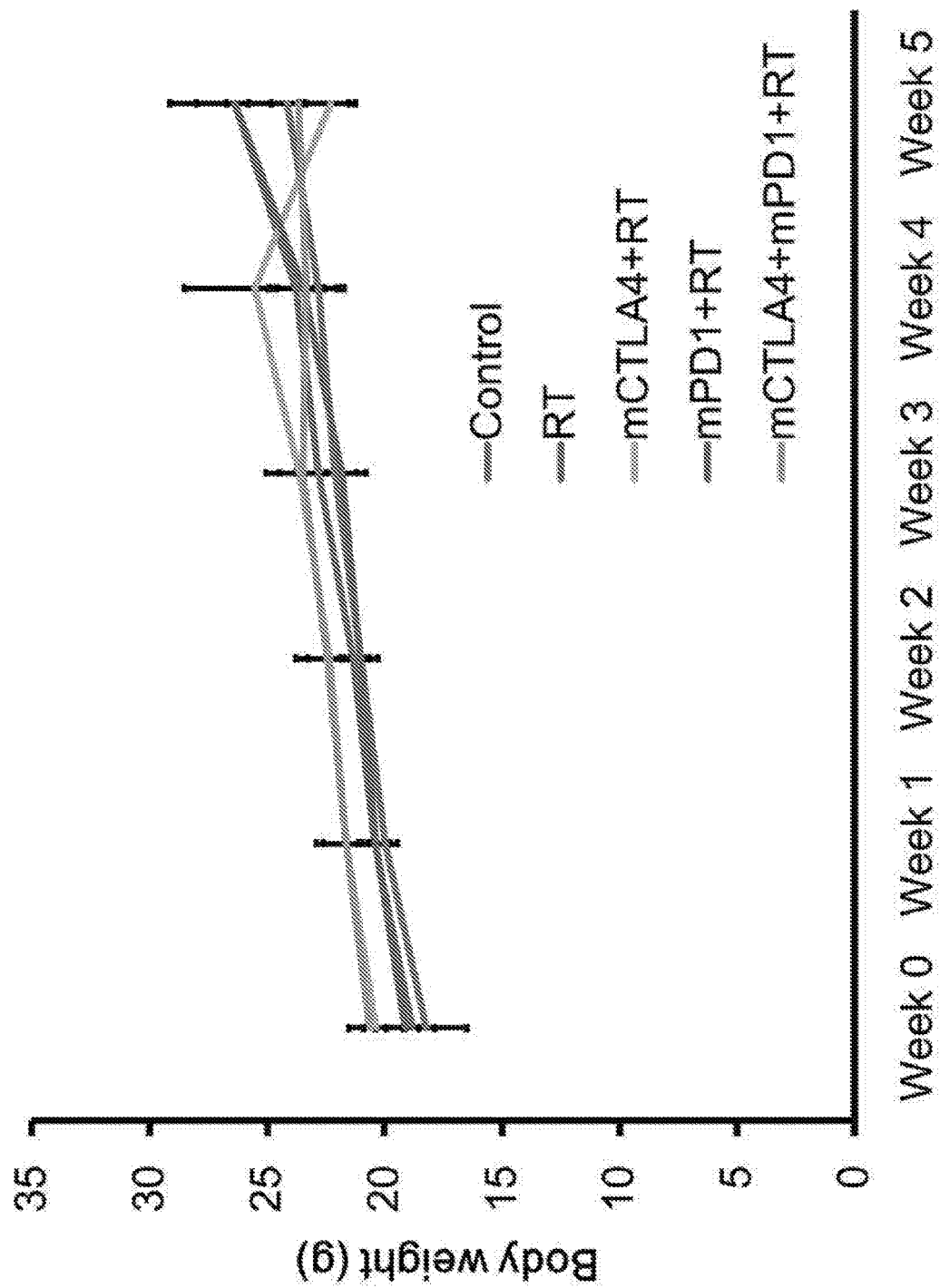
FIG. 1B shows the changes in body weight of B16 tumor-bearing mice treated with the radio treatment in Example 1.
Figure 1C:
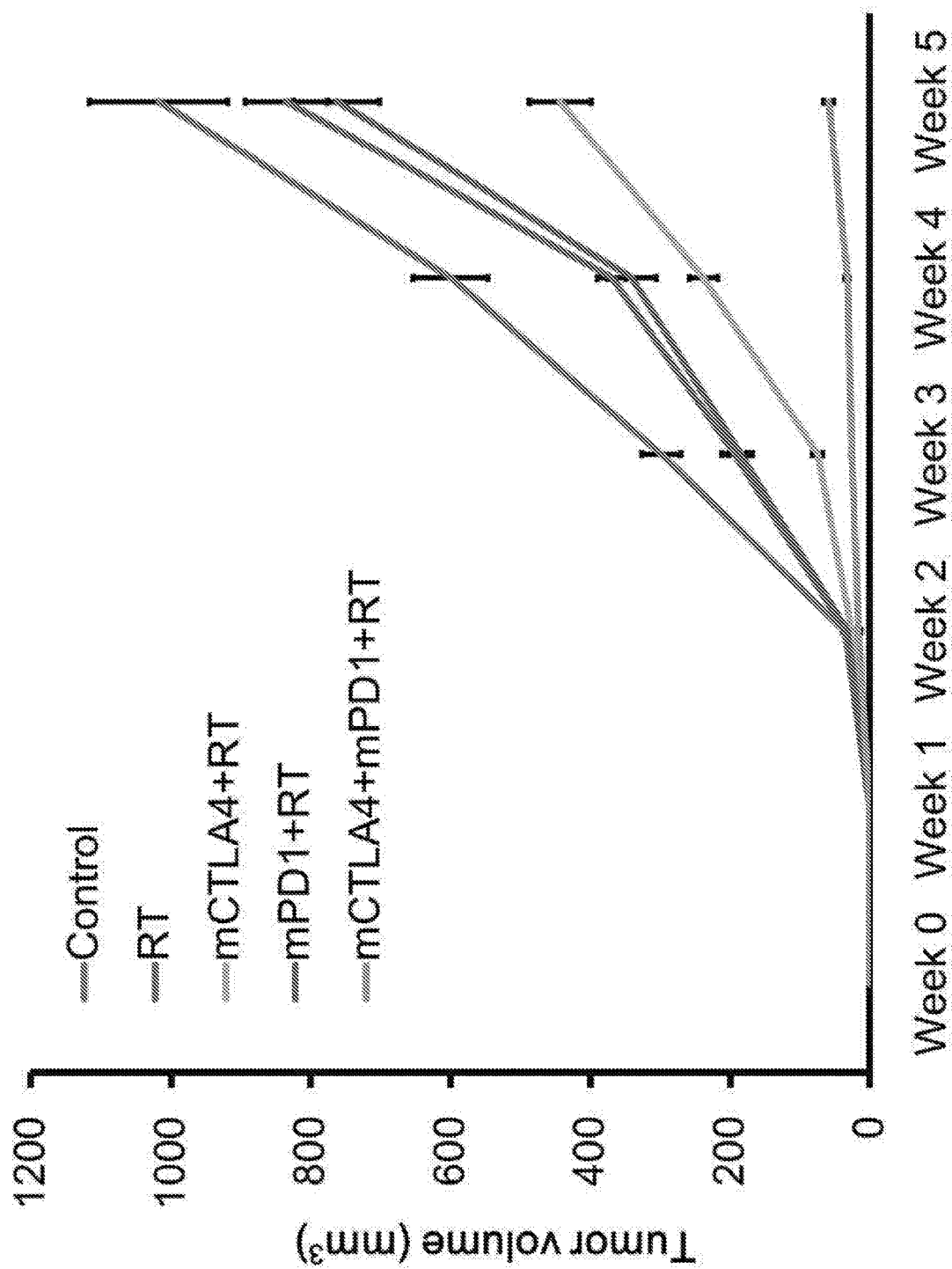
FIG. 1C shows the changes in body weight of B16 tumor-bearing mice in Example 1.

It was found that the mice vaccinated with the CTLA-4 or PD-1 DNA vaccines demonstrated increased antibody titers against respective proteins as compared with the control groups ($p<0.005$). As shown in FIG. 1B, the treatment of tumor bearing mice did not result in significant difference in body weights among experimental mice, indicating the lack of discernible toxicity. As compared with radiation alone, the radiotherapy in combination the treatment of the CTLA-4 vaccine led to more tumor regression (a 53.2% reduction of tumor volume; $p=0.125$) 1 month after radiation started. However, immunization with PD-1 vaccine did not significantly enhance the tumor suppression of radiation (a 14.7% reduction of tumor volume; $p=0.55$). It was also observed that at the end of the experiment, the tumors were significantly suppressed in the tumor bearing mice treated with the radiation plus the CTLA-4 and PD-1 vaccines as compared with other groups. As shown in FIG. 1C, near total regression of B16F10 tumors was observed in the mice treated with radiation plus the both CTLA-4 and PD-1 vaccines, a 92.4% decrease of tumor volume relative to that of radiation alone group ($p=0.037$).

EXAMPLE 2

Combination Therapy of Radiation Plus DNA Vaccines Targeting CTLA-4 and PD-1 for Colorectal Cancer The Balb/c mice (5 mice per group) were used for inoculation of $1\times10^6$ colorectal CT26 cancer cells. The treatment schedule of vaccination and radiotherapy is similar to that of the first experiment with B16 bearing mice, except that the mice were irradiation with 8 Gy per fraction (see FIG. 1A).

Figure 2A:
FIG. 2A provides a schema of experiment and treatment schedule in Example 2.
Figure 2B:
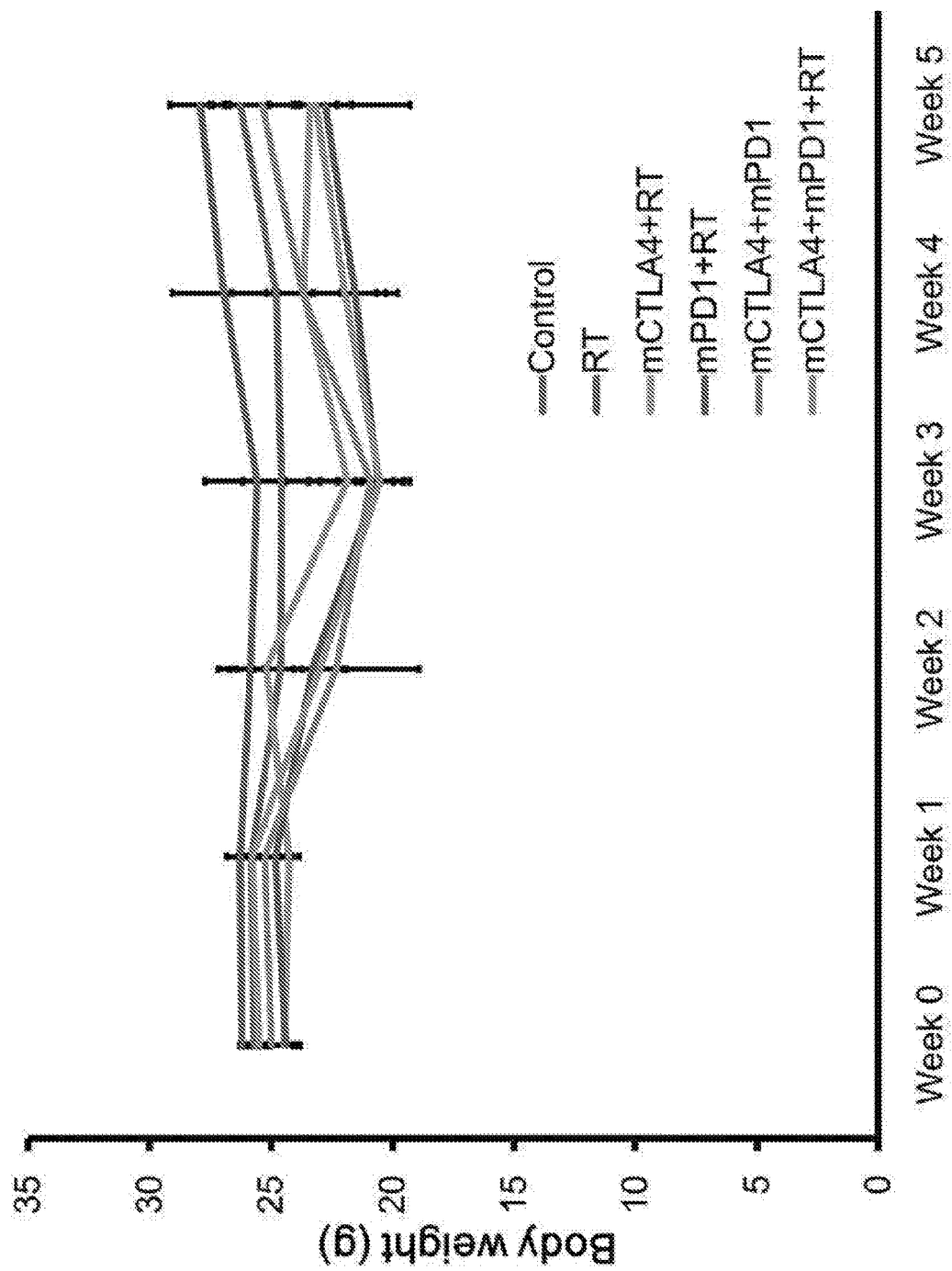
FIG. 2B shows the changes in body weight of CT26 tumor-baring mice in Example 2.
Figure 2C:
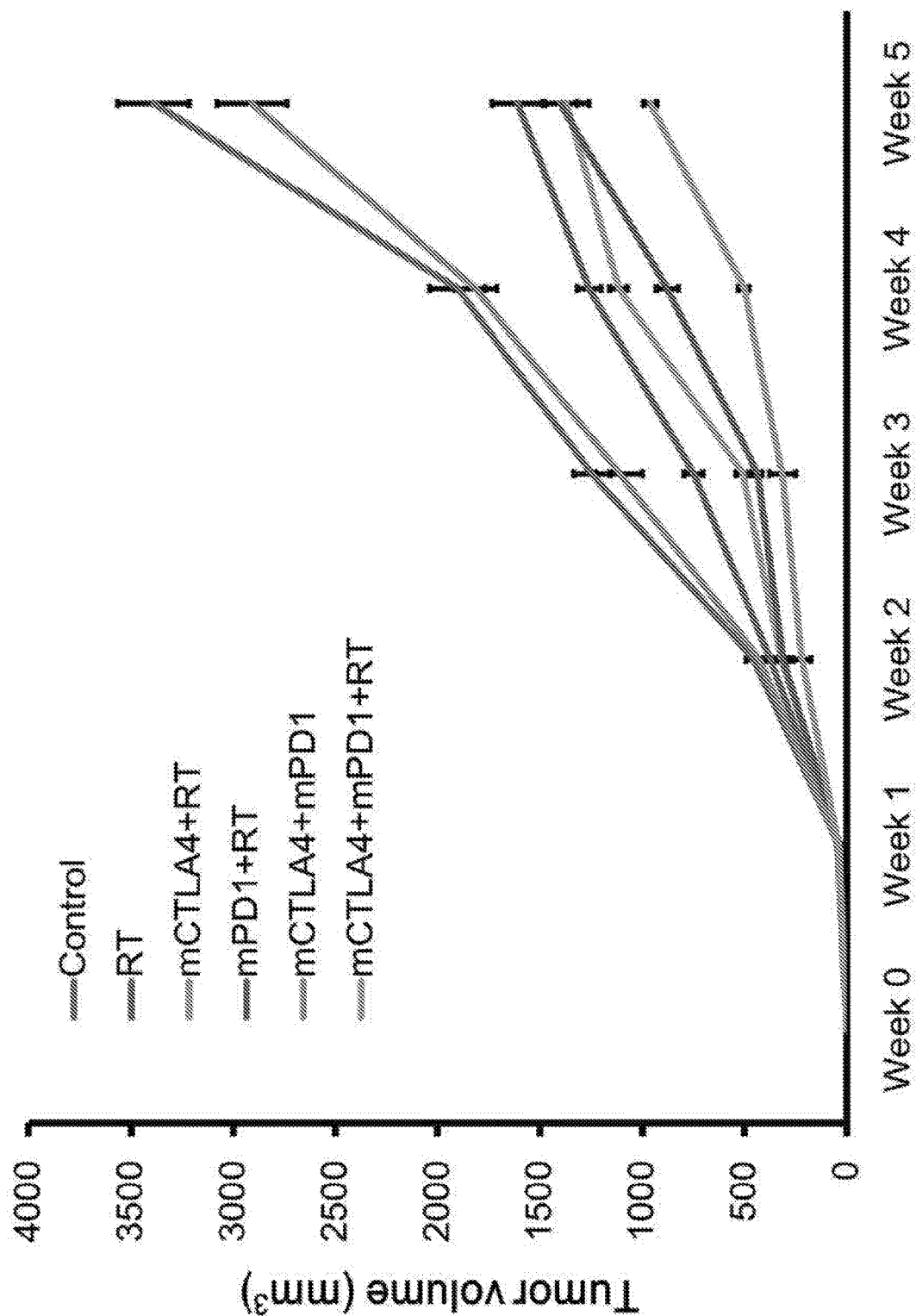
FIG. 2C shows the CT26 tumor suppression by various treatment strategies in Example 2.

As shown in FIG. 2B, there was no significant difference in body weights among experimental mice treated with various regimens. The results of anticancer effects of different treatment strategies were also similar to those in Example 1, showing most significant tumor suppressive effect by the radiotherapy in combination of the treatment of both CTLA-4 and PD-1 DNA vaccines, among the treatment groups (p<0.01). In particular, the mice treated with radiation in combination the both CTLA-4 and PD-1 vaccine exhibited better tumor suppressive effect than the group treated with radiotherapy with either CTLA-4 vaccine (p=0.003) or PD1 DNA vaccine (p=0.001). It was also observed that at the end of the experiment, the tumors were significantly suppressed in the tumor bearing mice treated with the radiation plus the CTLA-4 and PD-1 vaccines as compared with other groups.

EXAMPLE 3

Figure 3A:
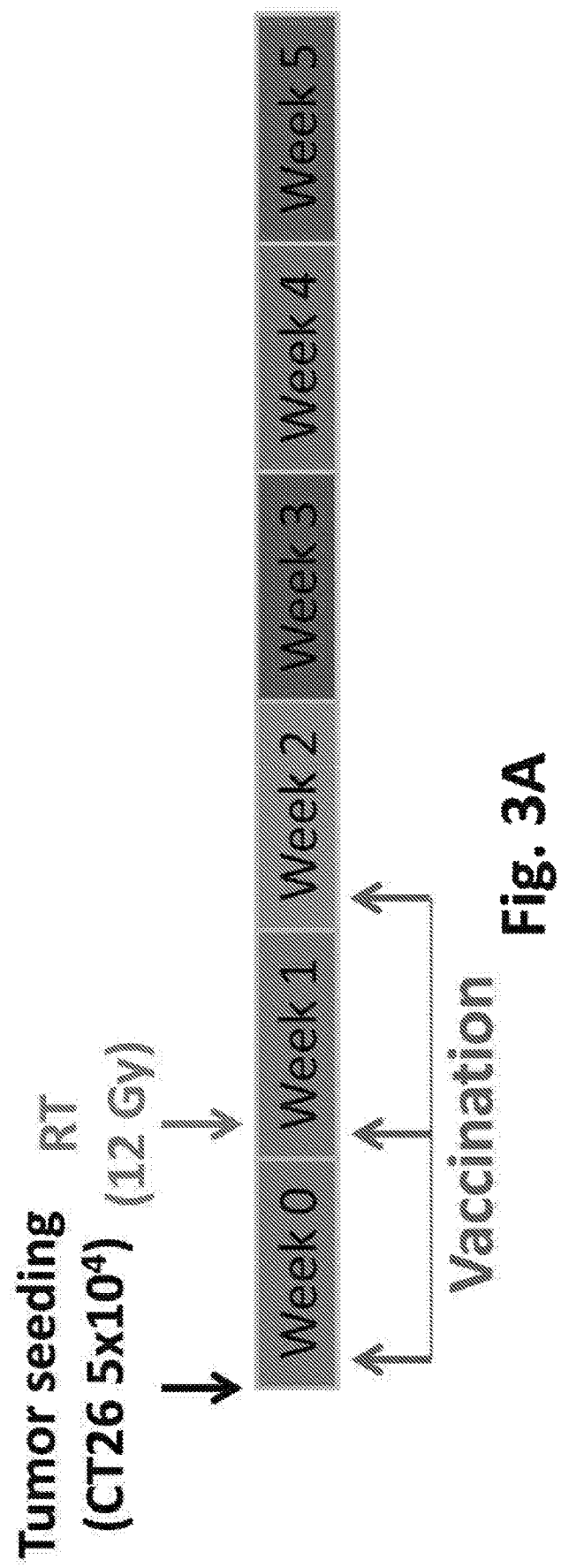
FIG. 3A shows a schema of experiment and treatment schedule on CT26 tumor suppression in Example 3.

Combination Therapy of Radiation Plus DNA Vaccines Targeting CTLA-4 and PD-L1 for Colorectal Cancer We examine the effect of CTLA-4 and PD-L1 DNA vaccines in combination with radiotherapy on CT26 tumor growth in vivo. This experiment was conducted similarly to Example 2, except that the PD-1 DNA vaccine was replaced for the PD-L1 DNA vaccine, and mice were treated radiotherapy only once with 12 Gy as illustrated in FIG. 3A.

Figure 3B:
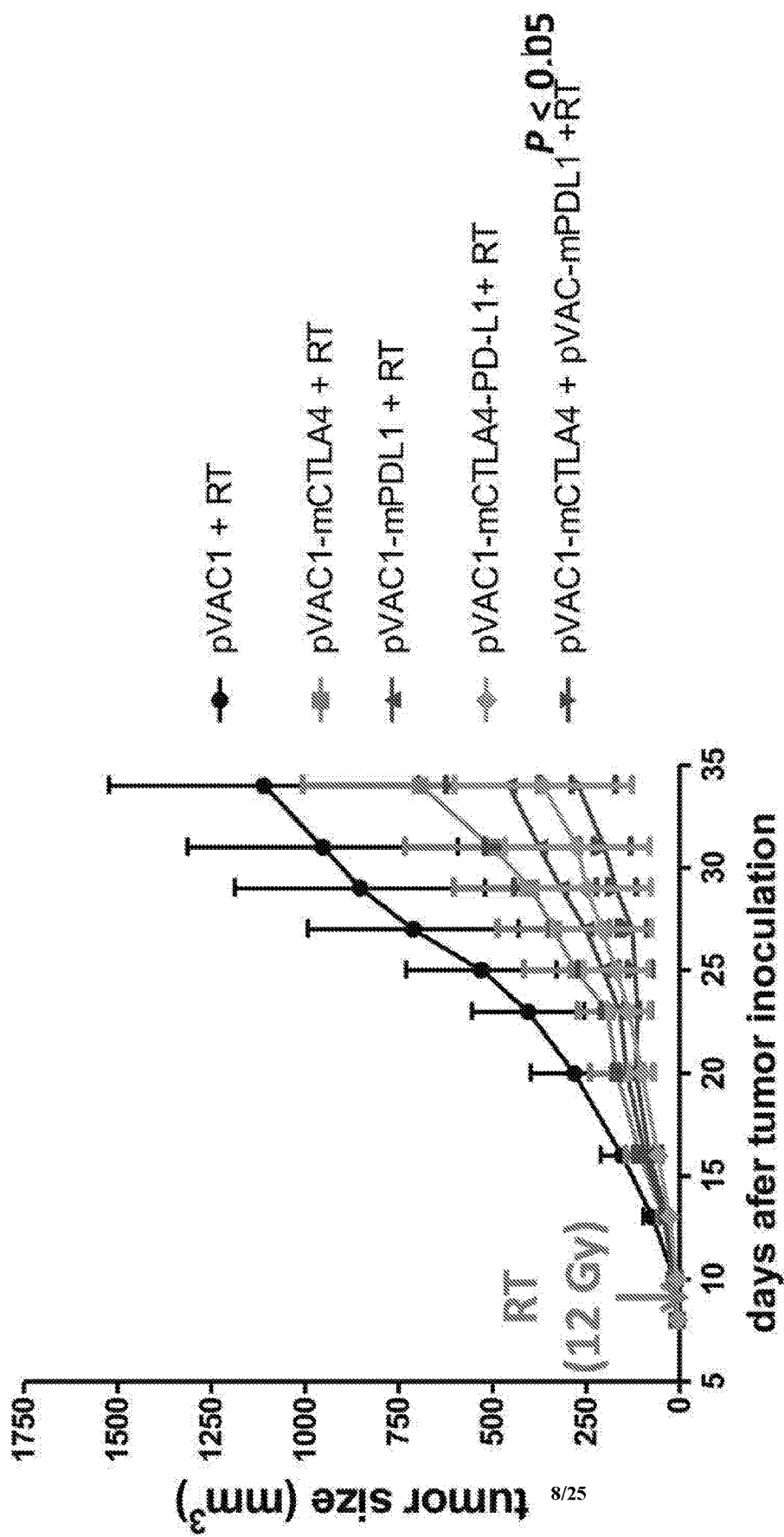
FIG. 3B shows the CT26 tumor suppression by various treatment strategies in Example 3, wherein the mice treated with a radiotherapy in association of the combination of the DNA vaccine of CTLA4 (pVAC1-mCTLA4) and the DNA vaccine of PDL1 (pVac1-mPDL1) reached statistic significance +RT in terms of tumor suppressive effect as compared with the mice treated with a radiotherapy in association of the vaccine of pVAC1.

The anticancer effects of different treatment strategies were also similar to those in Example 2, showing most significant tumor suppressive effect in the mice treated with radiotherapy in combination of the both CTLA-4 and PD-L1 DNA vaccines. As shown in FIG. 3B, there was no significant anticancer effect observed in the groups treated with the only single DNA vaccine, either CTLA-4 or PD-L1 in combination with radiotherapy, as compared with the group only treated by radiation; however as compared with the group treated with the radiation alone, the tumors were significantly suppressed in the group treated with radiation in combination with the both CTLA-4 and PD-L1 DNA vaccines, and the group with radiation plus the CTLA-4–PD-L1 fusion gene vaccine (p<0.05).

EXAMPLE 4

Figure 4A:
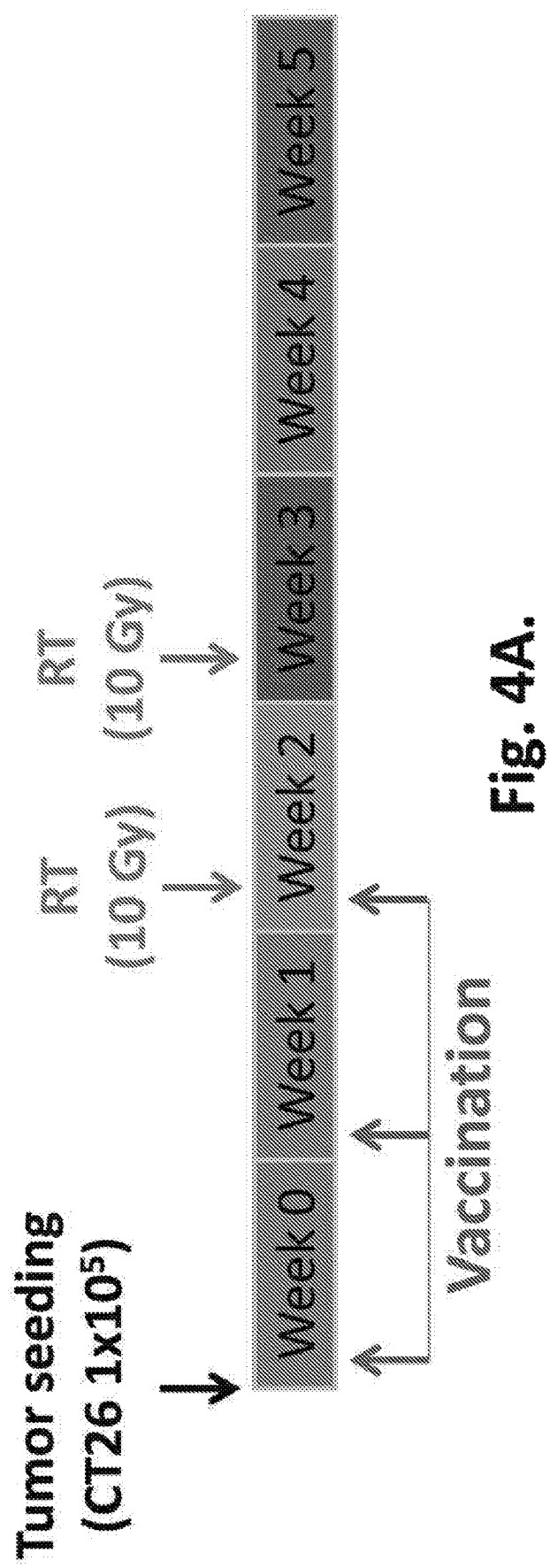
FIG. 4A shows a schema of experiment and treatment schedule on CT26 tumor suppression in Example 4.

Combination Therapy of Radiation Plus DNA Vaccines Targeting CTLA-4 and PD-L1 for Colorectal Cancer The liposomes coupled CTLA-4+PD-1 DNA vaccine and CTLA-4–PD-L1 fusion DAN vaccine were prepared respectively. The mice were inoculated with $1\times10^5$ cells and treated with two fractions of radiotherapy with 10 Gy each as illustrated in FIG. 4A, and treated with the liposomes.

Figure 4B:
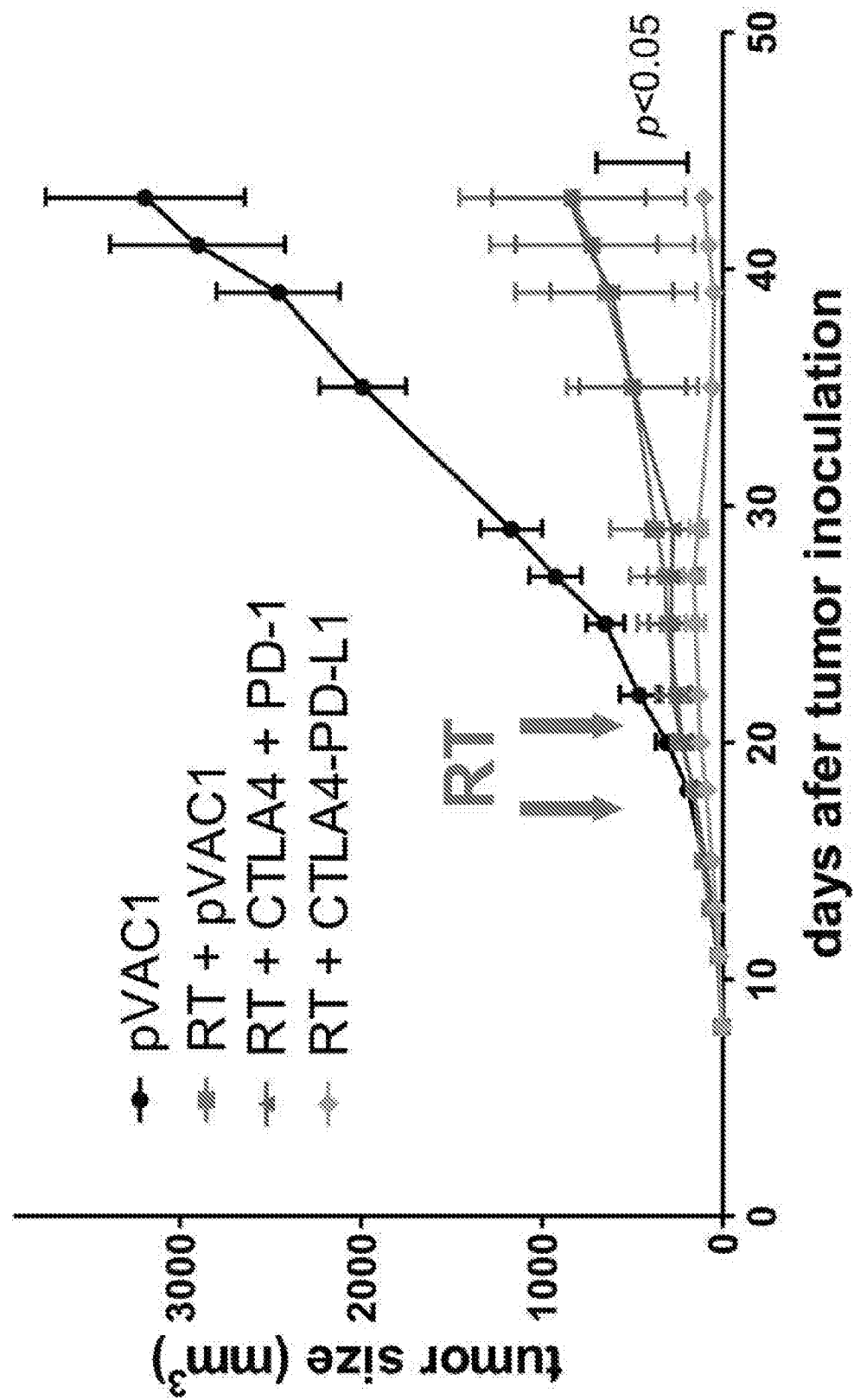
FIG. 4B shows the CT26 tumor suppression by various treatment strategies in Example 4, wherein the mice treated with the CTLA4-PLL1 (pVAC1-mCTLA4-mPDL1) vaccines in combination with radiotherapy (10 Gy×2 on day 16 and 22) reached statistic significance compared with the control group treated with RT only in terms of tumor suppressive effect.

As shown in FIG. 4B, the most significant antitumor effect was achieved by the liposome coupled CTLA-4–PD-L1 DNA vaccine in combination with radiotherapy as compared with the group treated with radiation alone (p<0.05).

EXAMPLE 5

Combination Therapy of Radiation Plus DNA Vaccines Targeting PD-1 Fragment (PD1 Frag), CTLA-4–PD-L1 (CTLA4–PDL1 Elec), or CTLA-4–PD-L1 Fusion Protein Vaccine for Colorectal Cancer The anticancer effects of PD-1 fragment DNA vaccine (PD1 Frag), CTLA-4–PD-L1 DNA vaccine (CTLA4–PDL1 Elec) and CTLA-4–PD-L1 protein vaccine (CTLA-4–PDL1 Prot) in combination with radiotherapy (RT) on CT26 tumor growth in vivo were investigated. This experiment design and treatment schedule were similar to Example 4, except that $5\times10^4$ instead of $1\times10^5$ CT26 cells were used to inoculate each mouse.

Figure 5A:
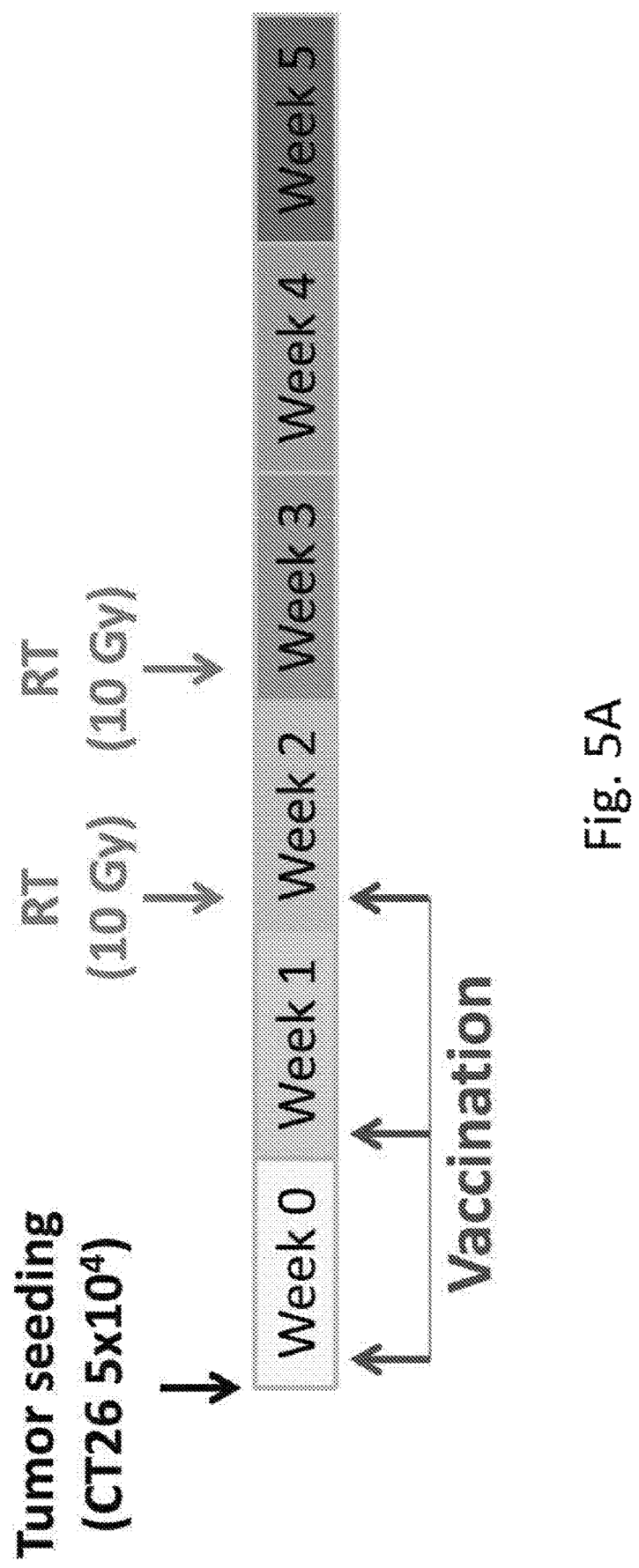
FIG. 5A shows a schema of experiment and treatment schedule on CT26 tumor suppression in Example 5.
Figure 5B:
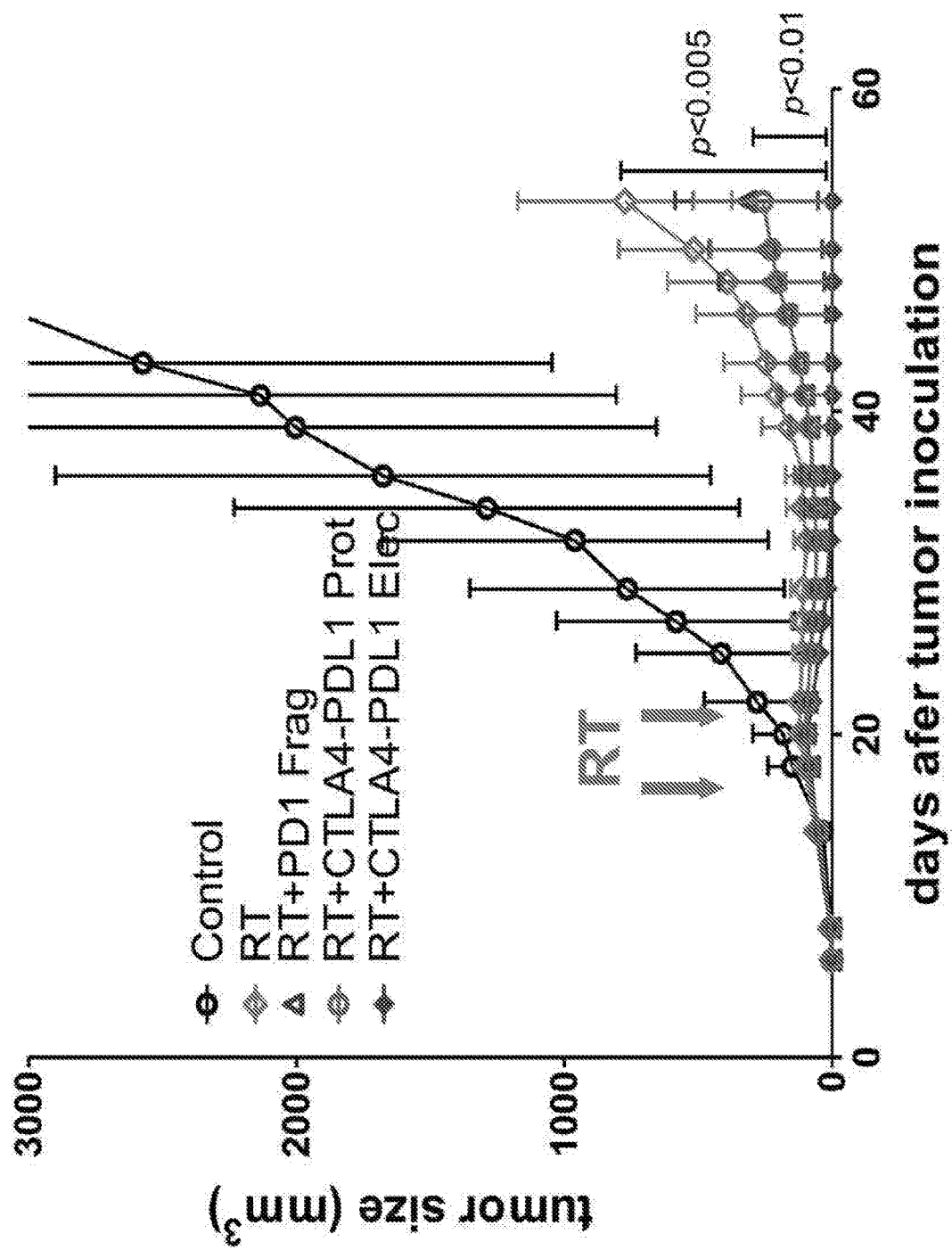
FIG. 5B shows the CT26 tumor suppression by radiation combined with various vaccines, including the DNA vaccine of CTLA4–PDL1 (pVAC1-mCTLA4–PDL1) delivered by electroporation in combination with radiotherapy reached statistic significance compared with pVAC1+RT and other vaccines in terms of tumor suppressive effect.
Figure 5C:
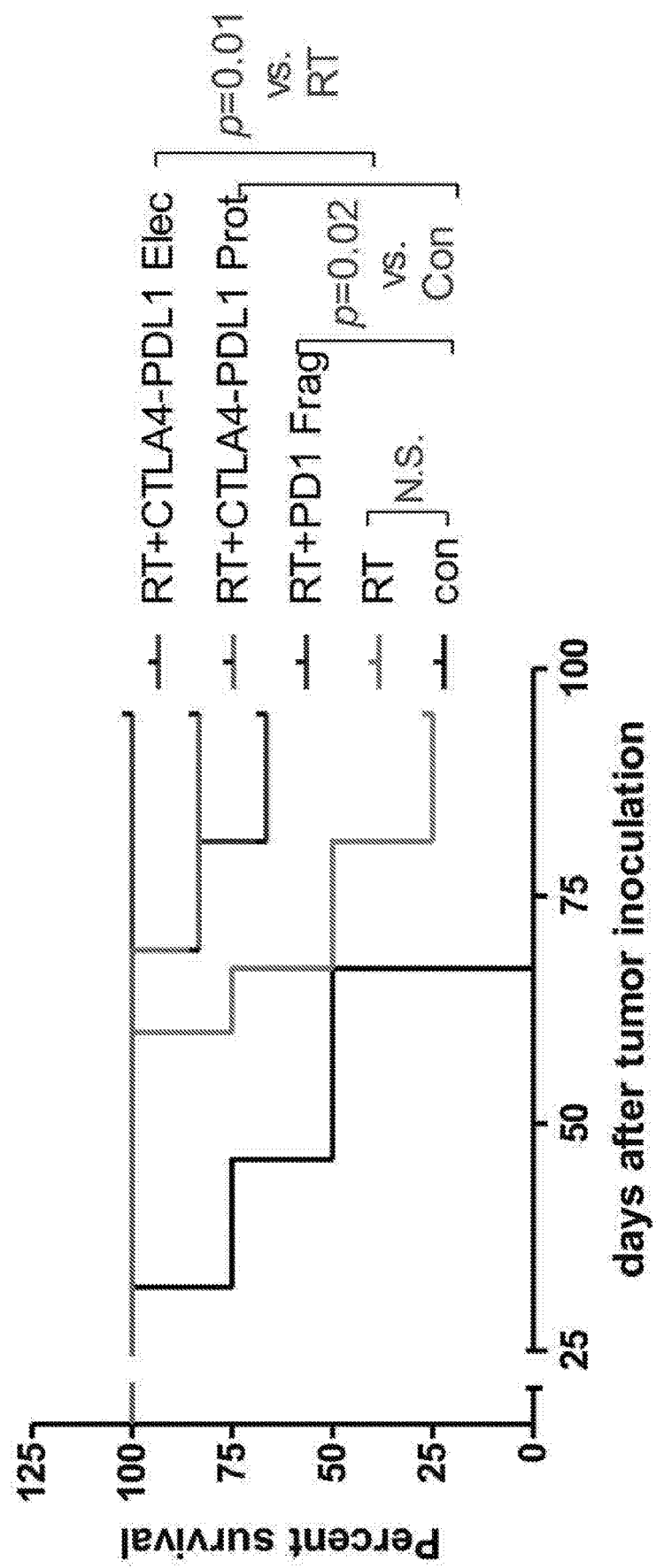
FIG. 5C shows the Kapin-Meier survival curves of mice treated with radiation in combination with various vaccines in Example 5.

In terms of the changes in sizes of the subcutaneously inoculated CT26, only the CTLA-4–PD-L1 DNA vaccine showed statistically significance as compared with radiation treatment (FIG. 5B). As shown in FIG. 5B, the both CTLA-4–PD-L1 Prot vaccine and the PD1 Frag vaccine in combination of radiation (RT) provided better effects in the suppression of tumor growth, but there was no statistical significance as compared with that of RT alone. However as shown in FIG. 5C, the both CTLA4–PDL1 Prot vaccine and the PD1 Frag vaccine displayed statistical significance when combined with RT.

EXAMPLE 6

Abscopal Effect of the CTLA-4–PD-L1 Vaccine for Colorectal Cancer

Figure 6A:
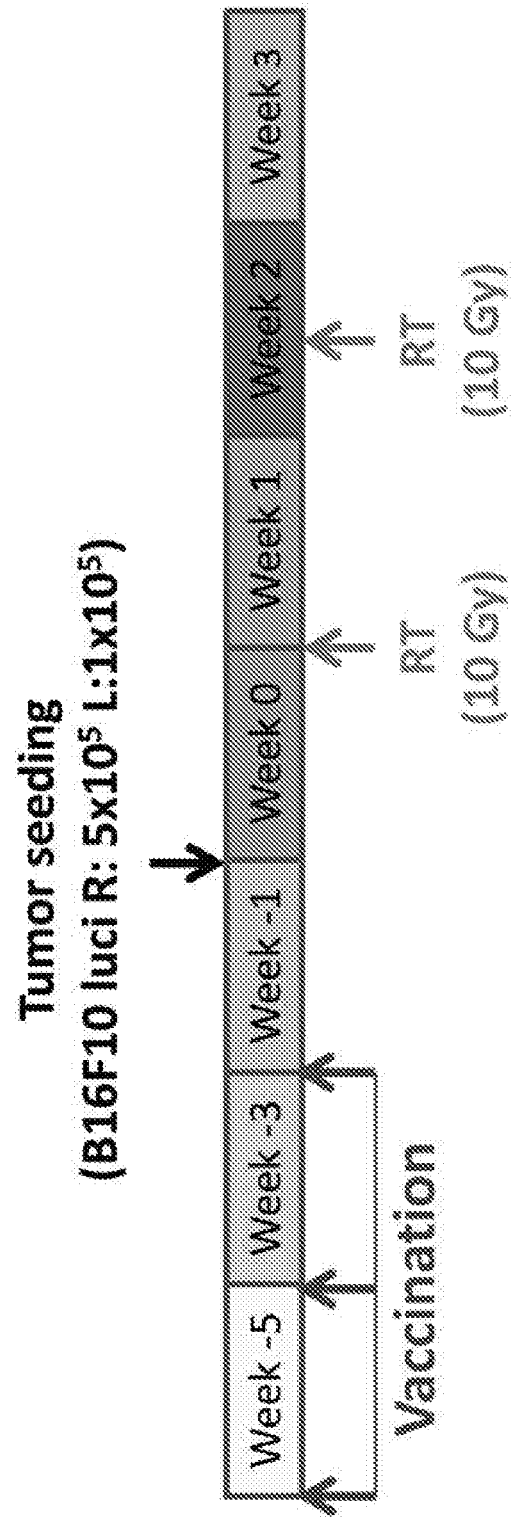
FIG. 6A shows a schema of experiment and treatment schedule on B16 tumor suppression in Example 6.

The anticancer effect of radiation on the un-irradiated tumors is so-called "abscopal effect". The CTLA-4–PD-L1 DNA vaccine or the protein vaccine were tested for the suppression of the tumor in this example. not only the irradiated tumor over right flanks of the experimental mice, but also the un-irradiated ones over the left flanks. The immune checkpoint vaccines can result in this rarely seen but very beneficial "abscopal effect" of radiation. The experimental design was illustrated in FIG. 6A.

As shown in FIG. 6B, the vaccines in combined with radiotherapy did not show further enhancement of anticancer effect of radiation but the CTLA-4–PD-L1 DNA vaccine inhibited the growth of un-irradiated tumor inoculated over the left flanks of the mice, indicating that the CTLA-4–PD-L1 DNA vaccine was capable of inducing the abscopal effect of radiation.

EXAMPLE 7

Figure 7A:
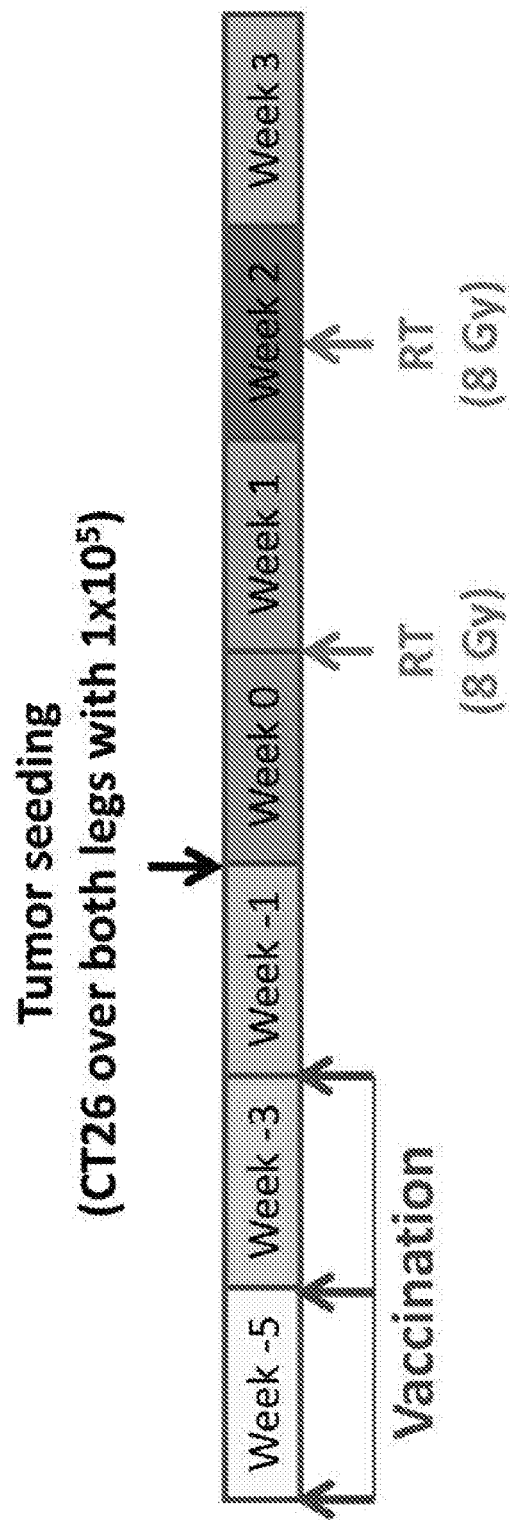
FIG. 7A shows a schema of experiment and treatment schedule on CT26 tumor suppression in Example 7.

Abscopal Effect of Radiotherapy in Combination of the Vaccines Targeting CTLA-4 and PD-1 in Colorectal Cancer The abscopal effect was demonstrated in CT26 tumor models treated with the various DNA vaccines in combination with radiation. The experimental design was illustrated in FIG. 7A. The Balb/c mice were inoculated with CT26 colon tumors on both legs, followed by injection of indicated anti-CTLA-4 (mCTLA) and/or anti-PD-1 (mPD1) DNA vaccines. RT: irradiation to the tumor on the right leg when indicated.

Figure 7B:
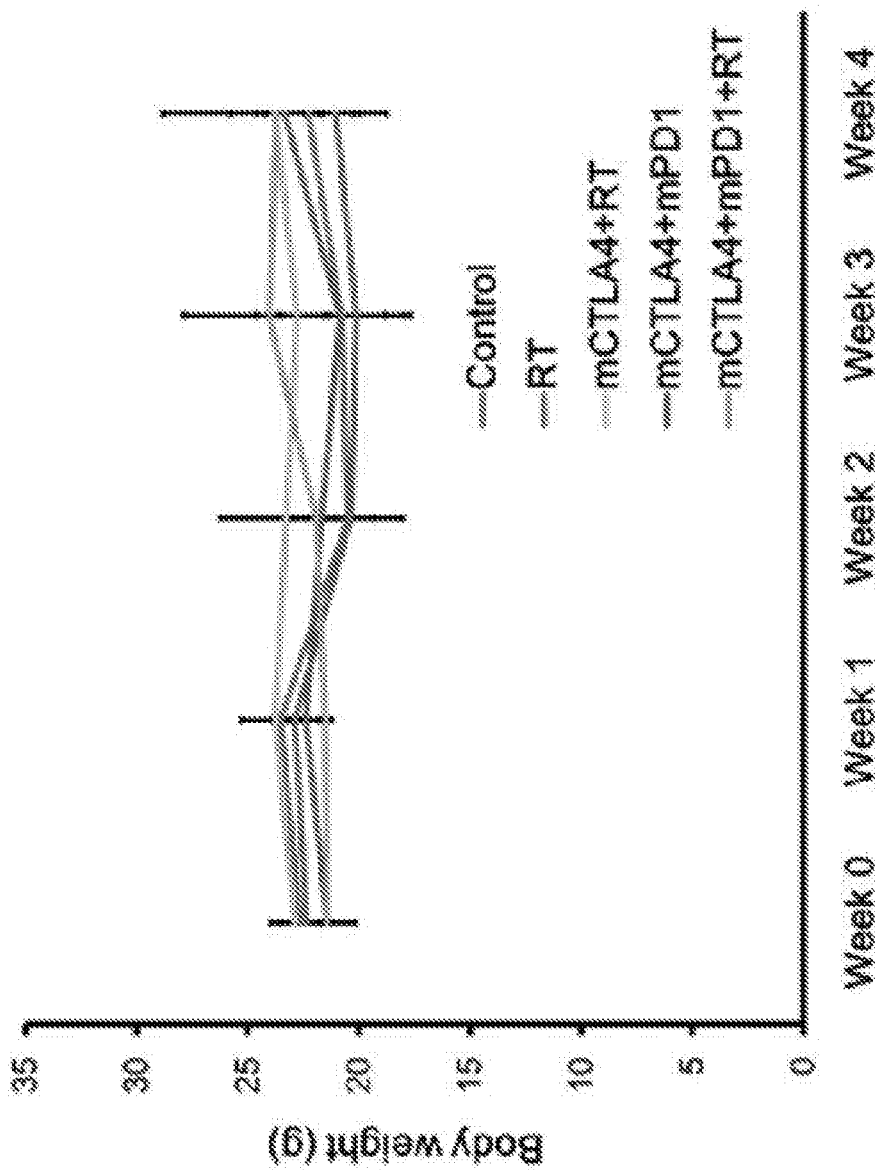
FIG. 7B shows the body weight changes in the groups treated with the DNA vaccine wherein the Balb/c mice were inoculated with CT26 colon tumors on both legs, following injection of indicated anti-CTLA-4 (mCTLA) and/or anti-PD-1 (mPD1) DNA vaccines and irradiation to tumors on the right legs.
Figure 7C:
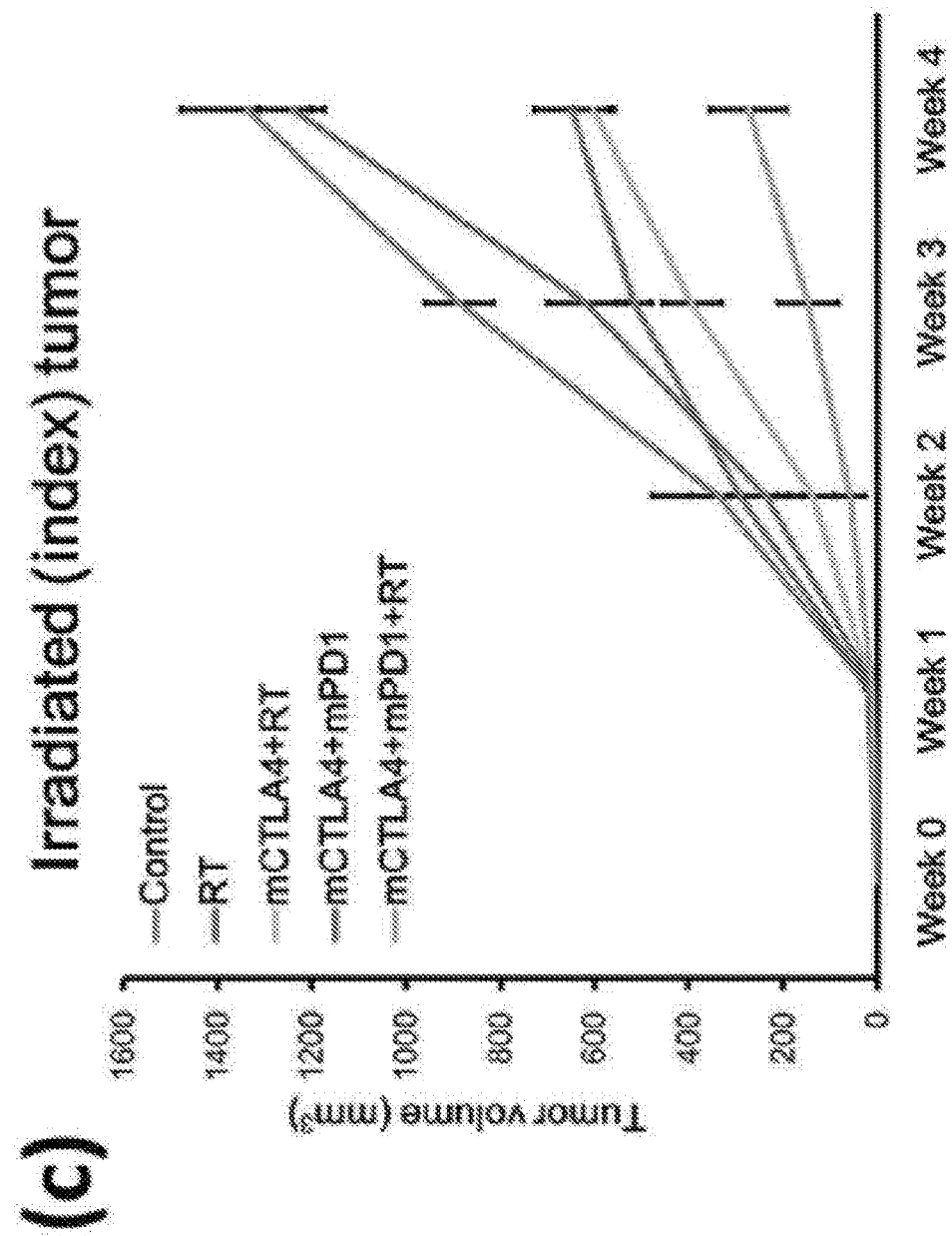
FIG. 7C shows the abscopal effect on irradiated tumor of the mice in Example 7.

As shown in FIG. 7B, there was no obvious difference in average body weight found between the treatment groups. The average tumor growth of the irradiated (index) tumors per group were shown in FIG. 7C, and the unirradiated tumors in FIG. 7D. Similar to the results observed in Example 6, the irradiated (index) CT26 tumors on the Balb/c mice receiving combined treatment with radiation and both immune checkpoint DNA vaccines showed an improvement in tumor regression as compared with the group treated with radiation alone. As observed in the groups treated with radiation plus the vaccines, there was significant regression in tumor, indicating the enhanced abscopal effect.

EXAMPLE 8

Figure 8A:
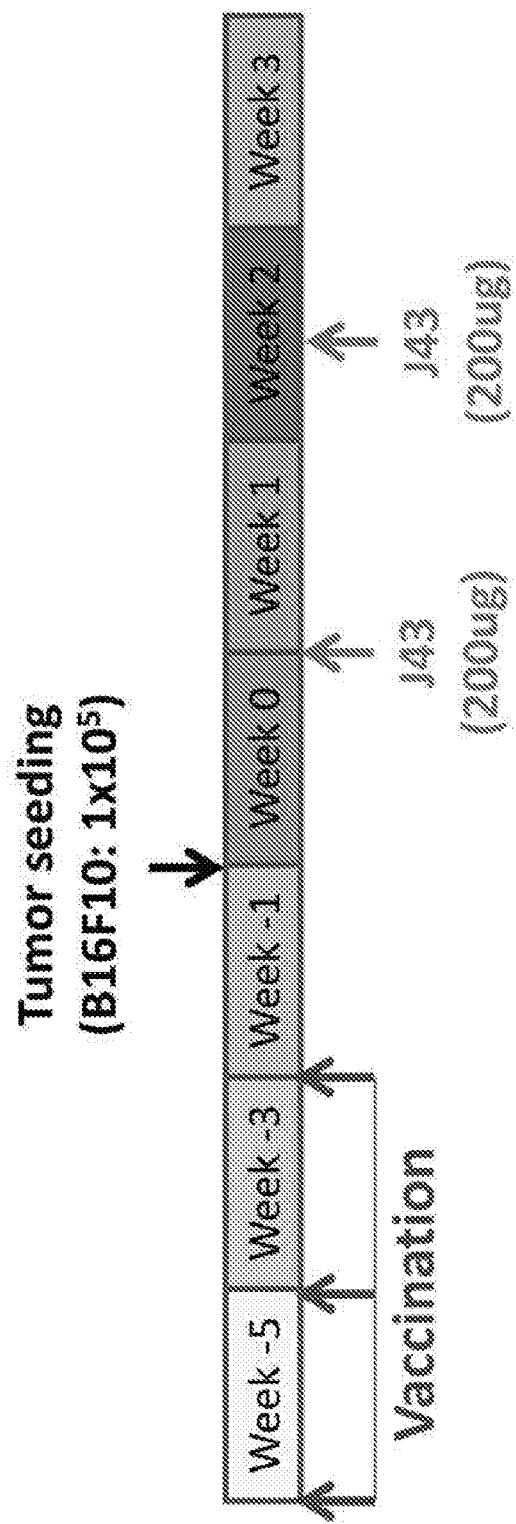
FIG. 8A shows a schema of experiment and treatment schedule on B16 tumor treated with DNA or protein vaccines combined with anti-PD1 antibody, J43, in Example 8.

Effect of Anti-PD-1 Antibody Plus CTLA-4–PD-L1 DNA or Protein Vaccines on Suppression To test the synergistic effect of the CTLA-4–PD-L1 DNA or protein vaccines in combination of the anti-PD-1 antibody, J43, the treatment schedule was designed as that shown in FIG. 8A.

Figure 8B:
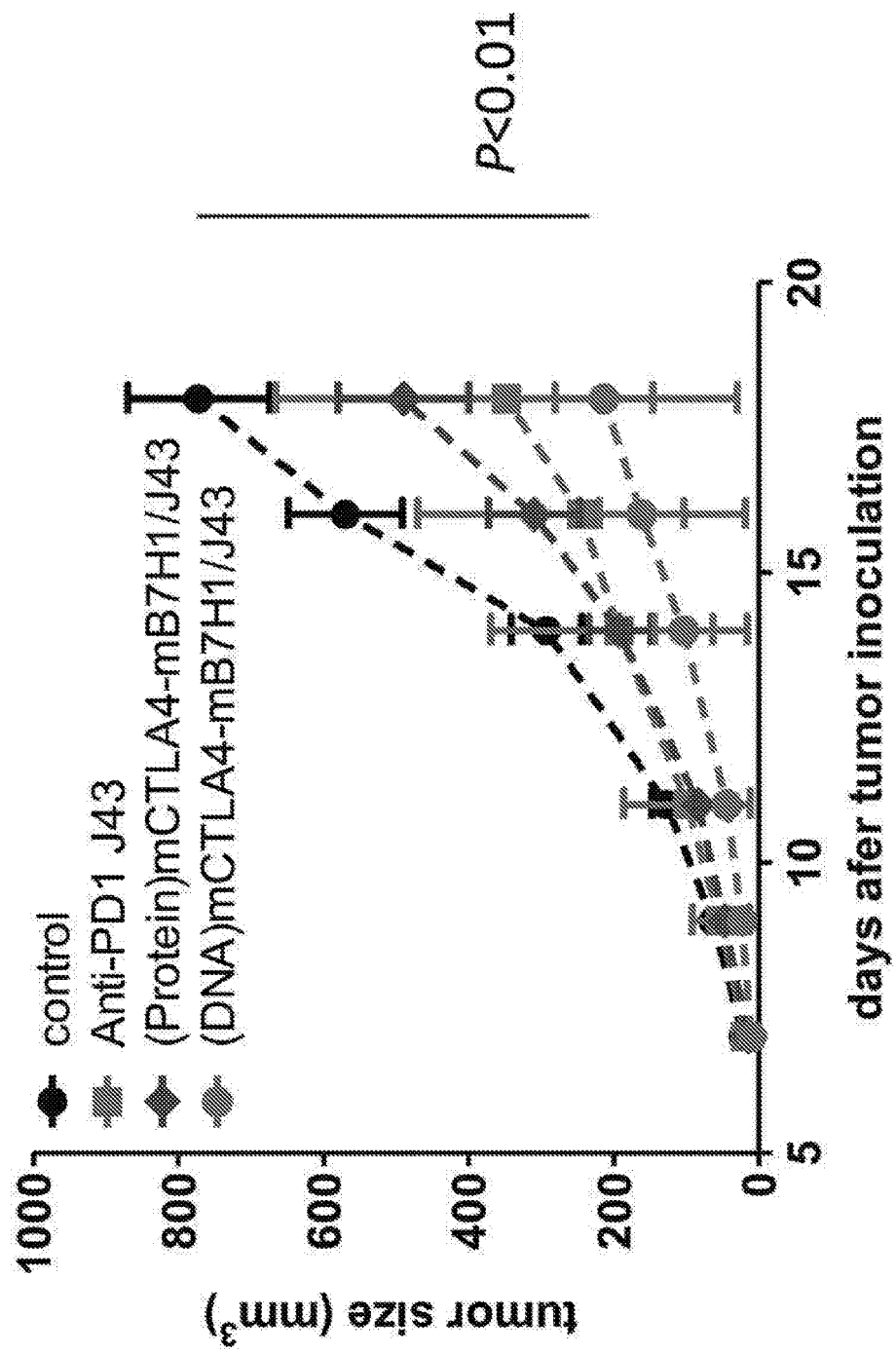
FIG. 8B shows the anticancer effect of the combination of J43 and CTLA-4–PD-L1 DNA vaccine in Example 8.

As shown in FIG. 8B, the combination of J43 and CTLA-4–PD-L1 DNA vaccine displayed superior anticancer effect as compared with the control group (p<0.01), while the anti-PD-1 antibody, J43, failed to demonstrate statistical significance in suppressing B16 tumor growth in vivo.

EXAMPLE 9

Figure 9A:
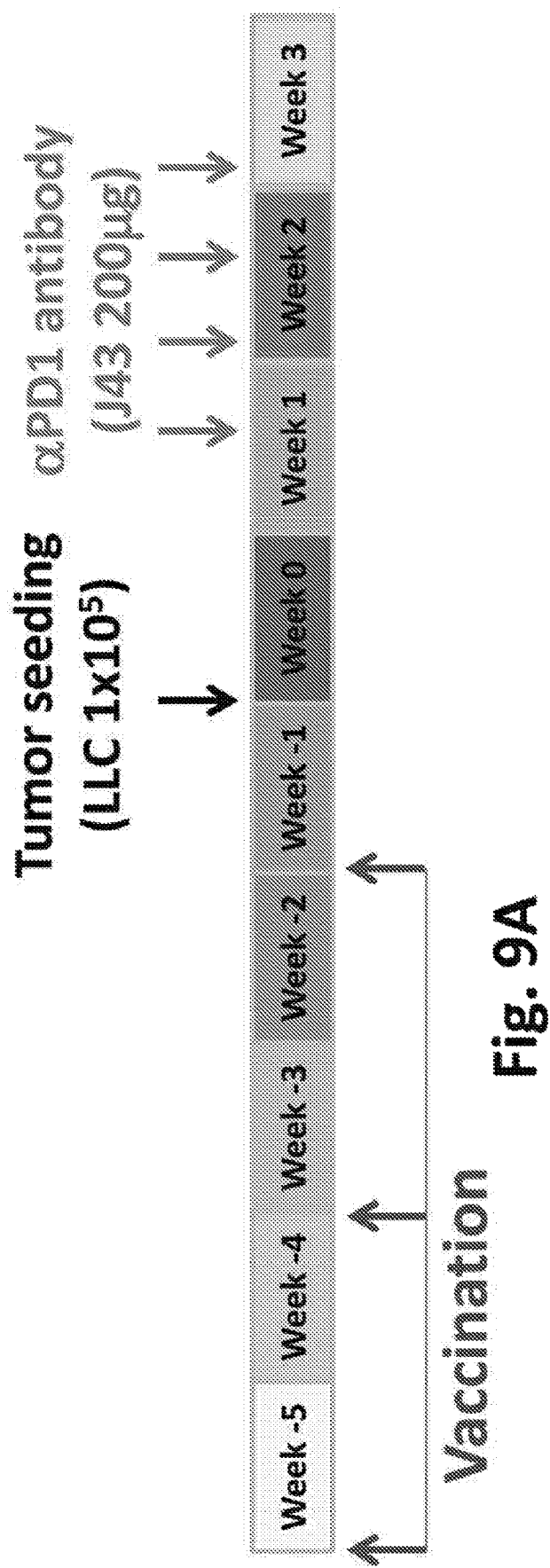
FIG. 9A shows a schema of experiment and treatment schedule on murine Lewis Lung Carcinoma (LLC) treated with DNA vaccines combined with anti-PD1 antibody (J43) in Example 9.

Effect of Anti-PD-1 Antibody Plus CTLA-4–PD-L1 DNA or Protein Vaccines on Suppression of Lung Cancer The anticancer effects of two different DNA vaccines, CTLA-4–PD-L1 and PD-1 fragments, and their combination, in the presence or absence of anti-PD-1 antibody, J43 were detected in Lewis lung cancer (LLC) cells. The experimental design and treatment schedule are shown in FIG. 9A.

Figure 9B:
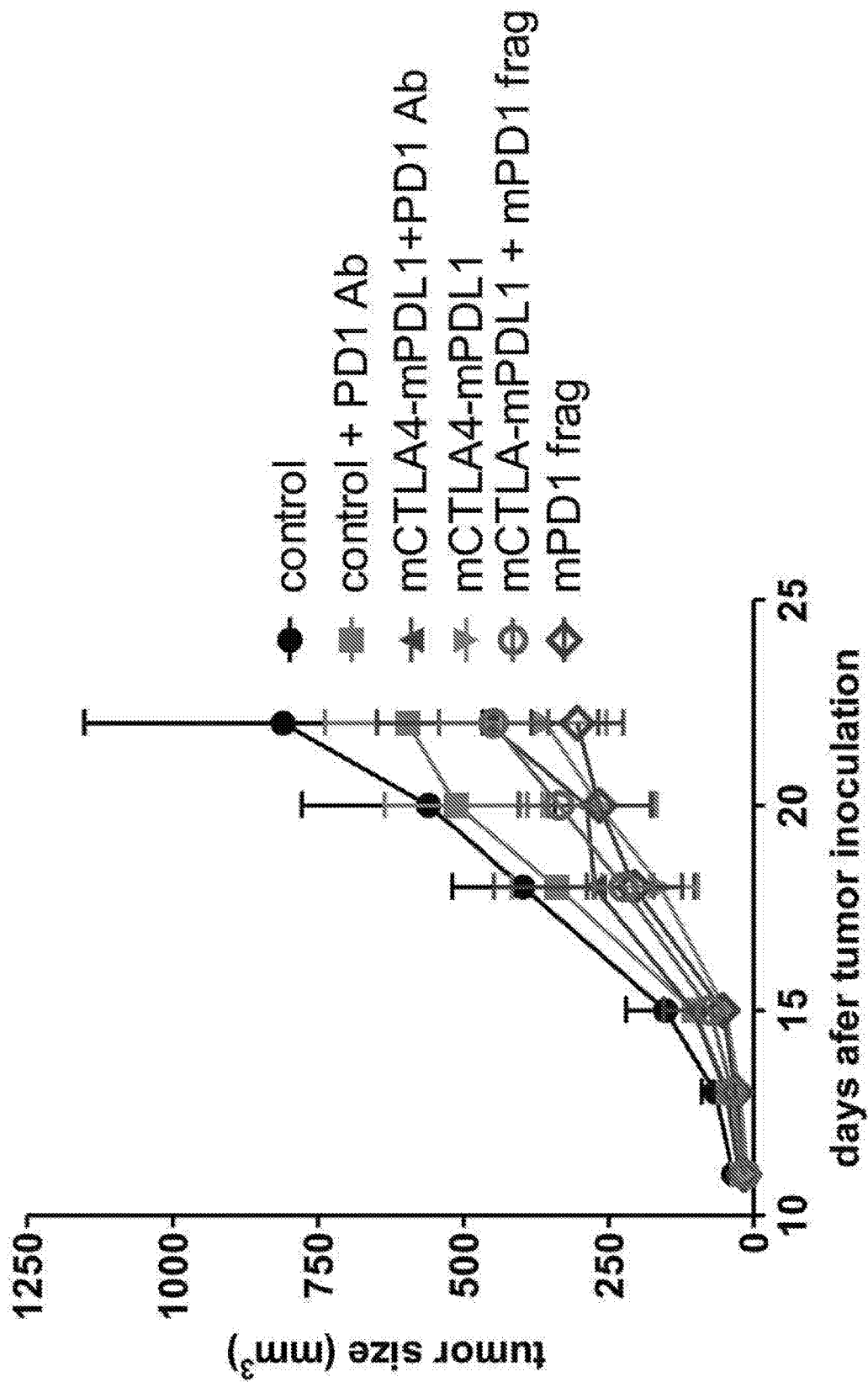
FIG. 9B shows the effect in inhibition of LLC growth by the CTLA-4–PD-L1 DNA vaccine either alone or in combination with J43, or PD-1 DNA fragments vaccine, or J43 alone.

Similar to the results in Example 8 using B16 melanoma model, anti-PD-1 antibody, J43, was not able to exhibit statistically significant suppression of Lewis lung carcinoma (LLC) growth. On the other hand, CTLA-4–PD-L1 DNA vaccine either alone or in combination with J43, or PD-1 DNA fragments vaccine, demonstrated significant inhibition of LLC growth as compared with control DNA or anti-PD1 antibody J43 alone (FIG. 9B). Additionally, PD-1 fragment DNA vaccine also displayed superior anticancer effect on LLC growth than J43, suggesting immune checkpoint DNA vaccine might work in human clinical settings as those approved antibodies. The statistic results were listed in Table 1.

TABLE 1

Statistic Results

| Newman-Keuls Multiple Comparison Test | Mean Difference | Significance (p < 0.05) | Summary |
|---|---|---|---|
| mCTLA4-mPDL1 vs control | −192.1 | p < 0.05 | ** |
| mCTLA4-mPDL1 vs control + PD1 Ab | −124.6 | p < 0.05 | * |
| mCTLA4-mPDL1 vs mCTLA4-mPDL1 + PD1 Ab | −54.82 | No | ns |
| mCTLA4-mPDL1 vs mCTLA-mPDL1 + mPD1 frag | −44.39 | No | ns |
| mCTLA4-mPDL1 vs mPD1 frag | −1.720 | No | ns |
| mPD1 frag vs control | −190.4 | p < 0.05 | ** |
| mPD1 frag vs control + PD1 Ab | −122.9 | p < 0.05 | * |
| mPD1 frag vs mCTLA4-mPDL1 + PD1 Ab | −53.10 | No | ns |
| mPD1 frag vs mCTLA-mPDL1 + mPD1 frag | −42.67 | No | ns |
| mCTLA-mPDL1 + mPD1 frag vs control | −147.7 | p < 0.05 | ** |
| mCTLA-mPDL1 + mPD1 frag vs control + PD1 Ab | −80.21 | No | ns |
| mCTLA-mPDL1 + mPD1 frag vs mCTLA4-mPDL1 + PD1 Ab | −10.43 | No | ns |
| mCTLA4-mPDL1 + PD1 Ab vs control | −137.3 | p < 0.05 | ** |
| mCTLA4-mPDL1 + PD1 Ab vs control + PD1 Ab | −69.78 | No | ns |
| control + PD1 Ab vs control | −67.52 | No | ns |

EXAMPLE 10

Figure 10A:
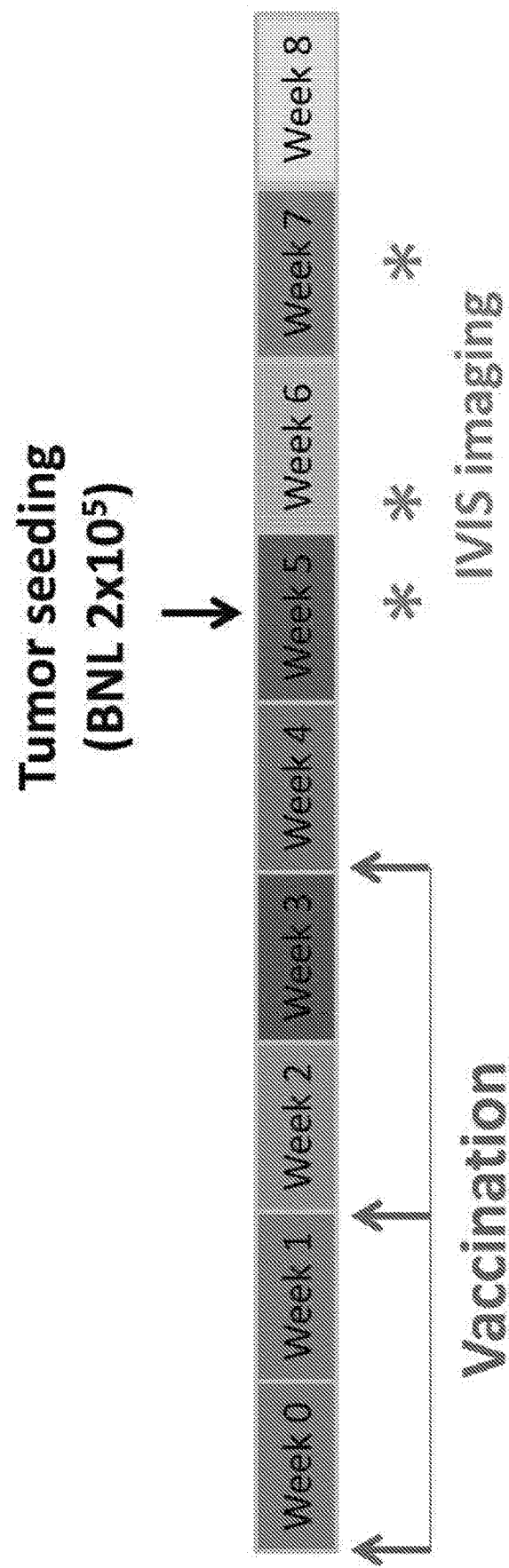
FIG. 10A shows a schema of experiment and treatment schedule on murine hepatocellular carcinoma (BNL) treated with mCTLA4–mPDL1 DNA vaccines in Example 10.

Effect of Anti-PD-1 Antibody Plus CTLA-4–PD-L1 DNA or Protein Vaccines on Suppression in Liver Cancer To test the effect of the CTLA-4–PD-L1 DNA vaccine on the growth of hepatocellular carcinoma cell (BNL) in vivo, the immunized BALB/c mice were subcutaneously inoculated with hepatic cell lines BNL/Luc ($2\times10^5$ cells/mouse) as indicated in FIG. 10A. The mice were imaged for luciferase activities, which represent the extent of tumor growth.

Figure 10B:
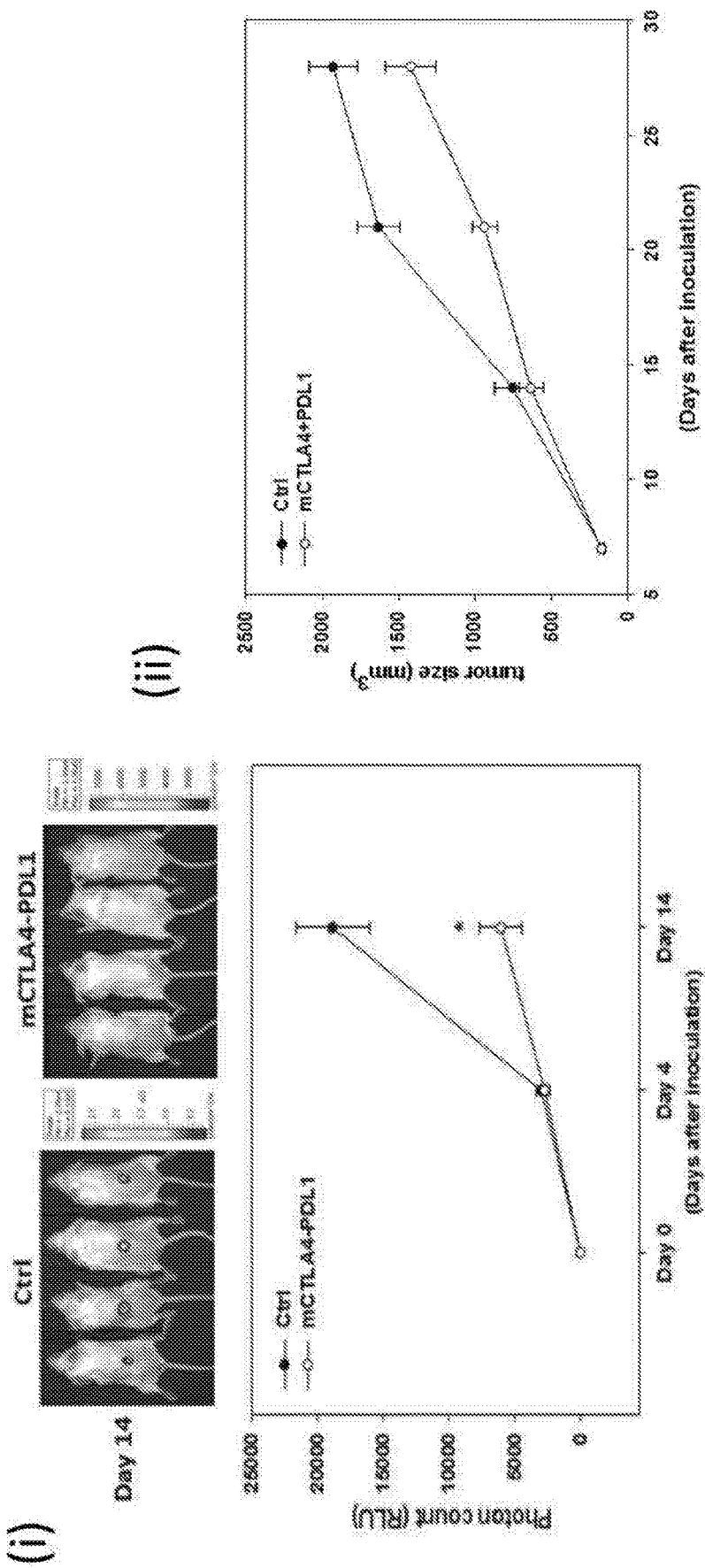
FIG. 10B shows the effect of the mCTLA4–PDL1 DNA vaccine on growth of BNL hepatoma cells in Exmple 10.

On Day 10 after the vaccination, the BALB/c mice were challenged with BNL/Luc hepatoma cells ($2*10^5$). The hepatocellular carcinoma in mice receiving pVAC-1 (control) and pVAC-1-mCTLA4–PDL1 were observed. As shown in FIG. 10B, there is no difference in average tumor growth between the treated group and the control group; however, suppressed tumor growth was exhibited in pVAC-1-mCTLA4–PDL1 immunized mice as compared with the control group (p<0.005).

Figure 7D:
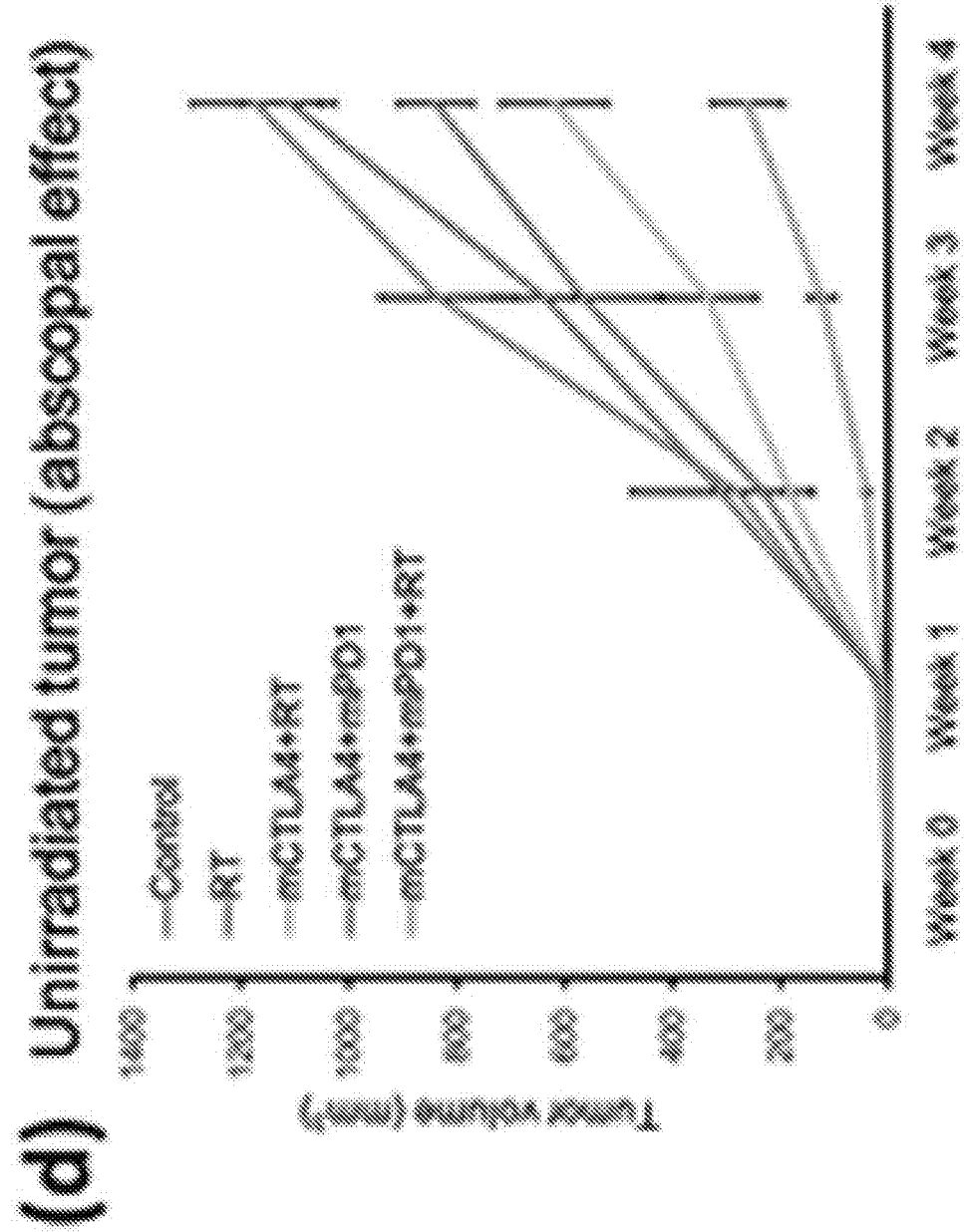
FIG. 7D shows the abscopal effect on un-irradiated tumor of the mice in Example 7.

It is concluded that the combination of DNA vaccines targeting CTLA-4, PD-1 or PD-L1 is potent for enhancing the combination of radiation or anti-PD-1 antibody in the suppression of tumor growth in vivo based on the following findings in the above mentioned examples:

(1) CTLA-4 or CTLA-4 plus PD-1 DNA vaccine can enhance the anticancer effect of radiation in B16 (FIG. 1B) and CT26 models (FIG. 2B);

(2) Both CTLA-4–PD-L1 fusion gene DNA and CTLA-4 plus PD-L1 DNA vaccines also demonstrated superior anticancer effect in combination with radiotherapy in CT26 model (FIG. 3B);

(3) Positive anti-CT26 effect was also observed when CTLA-4–PD-L1 DNA vaccine was delivered using liposome and radiation combined (FIG. 4B);

(4) Radiation enhanced survival of CT26 tumor bearing mice was achieved by not only CTLA-4–PD-1 DNA vaccine but also by its protein vaccine (FIG. 5B);

(5) CTLA-4–PD-L1 DNA vaccine can lead to abscopal effect in mice on B16 tumors which were not irradiated (FIG. 6B); similarly, in combination with radiotherapy, CTLA-4 plus PD-1 DNA vaccines achieved most significant abscopal effect on the unirradiated CT26 (FIG. 7D);

(6) Additionally, CTLA-4–PD-L1 DNA vaccine in combination with anti-PD1 antibody, J43, showed better anti-B16 effect as compared with J43 alone (FIG. 8B);

(7) Either CTLA-4–PD-L1 or PD-1 fragment DNA vaccine displayed better anti-LLC effect as compared with J43 alone (FIG. 9B); and (8) CTLA-4–PD-L1 DNA vaccine also exhibited inhibitory effect on hepatoma cell, BNL, growth in mice (FIG. 10B).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method for treating a malignant disease in a subject, comprising administering to said subject a vaccine in combination with a radiation treatment, in which the vaccine is a pharmaceutical composition comprising a DNA construct comprising a polynucleotide sequence encoding Cytotoxic T-lymphocyte antigen-4 (CTLA-4) and a PD-1 or a programmed cell death 1 ligand 1 (PD-L1), or combination thereof, wherein the malignant disease is colorectal cancer.

2. The method of claim 1, wherein the vaccine is a DNA vaccine comprising a polynucleotide sequence encoding CTLA-4 and PD-L1 or a DNA vaccine comprising a polynucleotide sequence encoding CTLA-4-PD-L1.

3. The method of claim 1, wherein the vaccine is a DNA vaccine comprising CTLA-4 and PD-1 or a DNA vaccine comprising CTLA-4-PD-1.

4. A method for treating a malignant disease in a subject, comprising administering to said subject a vaccine in combination with a radiation treatment, in which the vaccine is a pharmaceutical composition comprising a DNA construct comprising a polynucleotide sequence encoding Cytotoxic T-lymphocyte antigen-4 (CTLA-4), and a DNA construct comprising a polynucleotide sequence encoding PD-1 or a programmed cell death 1 ligand 1 (PD-L1), or combination thereof, wherein the malignant disease is colorectal cancer.

5. A method for treating a malignant disease in a subject, comprising administering to said subject a radiotherapy in association with a combination of a DNA construct comprising a polynucleotide sequence encoding CTLA-4, and a DNA construct comprising a polynucleotide sequence encoding PD-1 or PD-L1, wherein the malignant disease is colorectal cancer.

6. The method of claim 5, comprising administering to said subject a radiotherapy in combination of a DNA vaccine comprising a polynucleotide sequence encoding CTLA-4 and PD-1, or a DNA vaccine comprising a polynucleotide sequence encoding CTLA-4-PD-1.

* * * * *